(12) United States Patent
Rowan et al.

(10) Patent No.: US 7,754,272 B2
(45) Date of Patent: Jul. 13, 2010

(54) LOCAL DRUG DELIVERY

(75) Inventors: Lee Rowan, Warwickshire (GB); Peter William Stratford, Surrey (GB); Alistair Stewart Taylor, Surrey (GB); Terrence Albert Vick, Surrey (GB)

(73) Assignee: Biocompatibles IK Limited, Surrey (GB)

(*) Notice: Subject to any disclaimer, the term of this patent is extended or adjusted under 35 U.S.C. 154(b) by 1688 days.

(21) Appl. No.: 10/842,416

(22) Filed: May 11, 2004

(65) Prior Publication Data

US 2004/0208985 A1 Oct. 21, 2004

Related U.S. Application Data

(62) Division of application No. 09/979,602, filed as application No. PCT/GB00/02087 on May 30, 2000, now Pat. No. 6,872,225.

(30) Foreign Application Priority Data

May 27, 1999 (EP) .................................. 99304140
Jun. 11, 1999 (EP) .................................. 99304584

(51) Int. Cl.
 *B05D 3/02* (2006.01)
 *A61F 2/06* (2006.01)
(52) U.S. Cl. ...................... 427/2.1; 427/2.14; 427/2.21; 427/2.24; 427/2.25; 427/372.2; 623/1.1; 623/1.45; 623/1.43; 623/1.44; 623/1.46
(58) Field of Classification Search ................. 623/1.1, 623/1.43–1.46; 427/2.1, 2.14, 2.21, 2.24, 427/2.25

See application file for complete search history.

(56) References Cited

U.S. PATENT DOCUMENTS 5,645,883 A 7/1997 Russell et al.

(Continued)

FOREIGN PATENT DOCUMENTS

DE 197 44 135 C 3/1999

(Continued)

OTHER PUBLICATIONS

McNair AM: "Using hydrogel polymers for drug delivery", Medical Device Technology, vol. 7, No. 10, 1996, pp. 16-22.

(Continued)

*Primary Examiner*—Timothy H Meeks
*Assistant Examiner*—Cachet I Sellman
(74) *Attorney, Agent, or Firm*—Sughrue Mion, PLLC

(57) ABSTRACT

An implant having a coating comprising a polymer matrix is swollen in a pharmaceutical solution whereby pharmaceutically active compound is imbibed into the polymer matrix. When the product is implanted, release of the pharmaceutically active compound from the coating takes place. The polymer is preferably formed from ethylenically unsaturated monomers including a zwitterionic monomer, most preferably 2-methacryloyloxyethyl-2'-trimethylammoniumethylphosphate inner salt. The monomers from which the polymer is formed may further include surface binding monomers, such as hydrophobic group containing monomers, and crosslinkable monomers, the content of which may be used to control the swellability. Preferably the implant is a stent and the coating of polymer on the exterior wall surface is thicker than the coating of polymer on the interior surface. Release of the drug may be controlled by selection of comonomers. The implant is suitably a stent for use in the cardiovascular system.

62 Claims, 4 Drawing Sheets

U.S. PATENT DOCUMENTS

| | | | |
|---|---|---|---|
| 5,879,697 A | 3/1999 | Ding et al. | |
| 6,251,136 B1 | 6/2001 | Guruwaiya et al. | |
| 6,251,964 B1 * | 6/2001 | Porssa et al. | 523/105 |
| 6,461,631 B1 | 10/2002 | Dunn et al. | |
| 6,528,080 B2 | 3/2003 | Dunn et al. | |
| 6,746,686 B2 * | 6/2004 | Hughes et al. | 424/425 |

FOREIGN PATENT DOCUMENTS

| | | |
|---|---|---|
| EP | 0 897 701 A | 2/1999 |
| WO | WO 92 11896 A | 7/1992 |
| WO | WO 93/01221 A | 1/1993 |
| WO | WO 94/21308 A | 9/1994 |
| WO | WO 98/22516 | 5/1998 |
| WO | WO 98/30615 A | 7/1998 |
| WO | WO 9830615 A1 * | 7/1998 |
| WO | WO 00/04999 A | 2/2000 |
| WO | WO 0101957 A1 * | 1/2001 |

OTHER PUBLICATIONS

Cumberland DC, et al.: "Biomimicry 1: PC" Seminars in Interventional Cardiology, vol. 3, No. 3-4, 1998, pp. 149-150.

McNair AM, et al.: "Drug delivery from novel PC hydrogels", Proceedings of the International Symposium on Controlled Release Bioactive Materials, vol. 22, 1995, pp. 338-339.

* cited by examiner

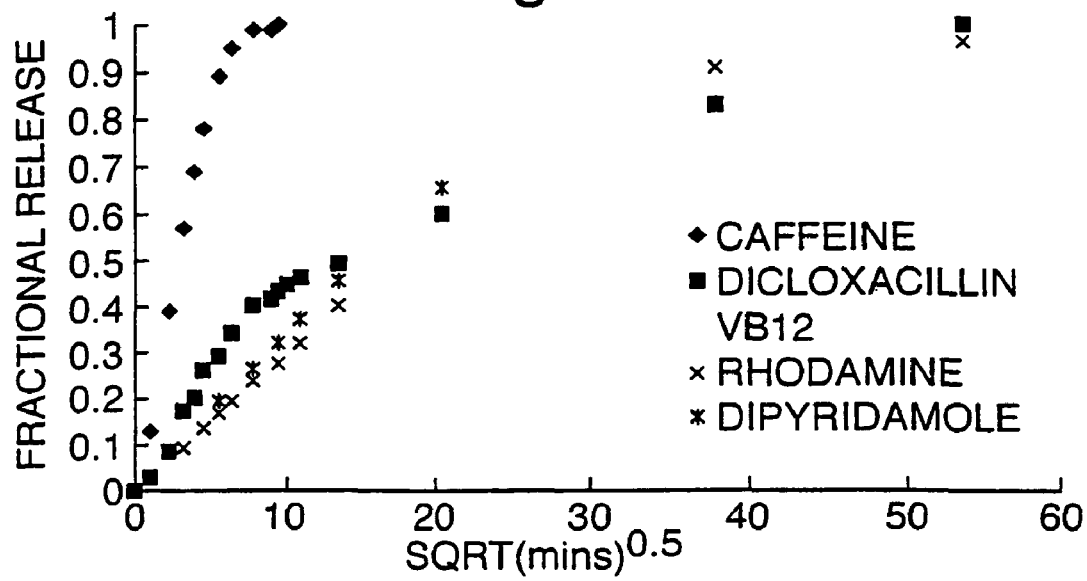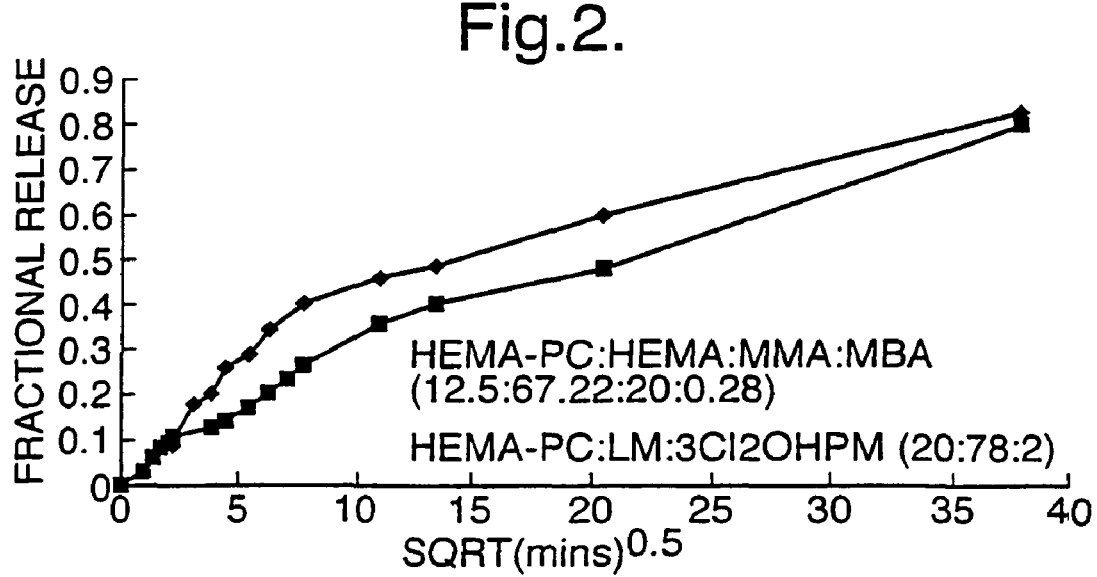

LOCAL DRUG DELIVERY

This application is a Divisional of U.S. application Ser. No. 09/979,602 filed Mar. 15, 2002 (now U.S. Pat. No. 6,872, 225); which is a 371 of PCT/GB00/02087, filed May 30, 2000; the disclosure of each of which is incorporated herein by reference.

The present invention relates to delivery of pharmaceutically active compounds by an implanted device to a lesion within the body. The device is preferably implanted in a body lumen, often effectively permanently implanted. The device is preferably a stent.

A leading cause of mortality within the developed world is cardiovascular disease. Coronary disease is of most concern. Patients having such disease usually have narrowing in one or more coronary arteries. One treatment is coronary stenting, which involves the placement of a stent at the site of acute artery closure. This type of surgery has proved effective in restoring vessel patency and decreasing myocardial ischemia. However the exposure of currently used metallic stents to flowing blood can result in thrombus formation, smooth muscle cell proliferation and acute thrombotic occlusion of the stent.

Non thrombogenic and anti thrombogenic coatings for stents have been developed. One type of balloon expandable stent has been coated with polymers having pendant zwitterionic groups, specifically phosphorylcholine (PC) groups, generally described in WO-A-93/01221. A particularly successful embodiment of those polymers suitable for use on balloon expandable stents has been described in WO-A-98/30615. The polymers coated onto the stent have pendant crosslinkable groups which are subsequently crosslinked by exposure to suitable conditions, generally heat and/or moisture. Specifically a trialkoxysilylalkyl group reacts with pendant groups of the same type and/or with hydroxyalkyl groups to generate intermolecular crosslinks. The coatings lead to reduced thrombogenicity.

Fischell, T A in Circulation (1996) 94: 1494-1495 describes tests carried out on various polymer coated stents. A thinner uniform polyurethane coating, having effectness of 23 μm was observed to have a better performance than a relatively non uniform thicker layer having a thickness in the range 75 to 125 μm. The thicker coatings are further described by Vander Giessen, W J et al in Circulation: 1996:94:1690-1697.

It has been suggested to utilise coatings on stents as reservoirs for pharmaceutically active agents desired for local delivery. WO-A-95103036 describes stents having a coating of an anti-angiogenic compound in a polymeric carrier. Examples of polymers are crosslinked ethylene-vinyl acetate copolymers, polycaprolactone and mixtures. In the worked examples, a stent is coated with a solution containing both polymer and pharmaceutically active compound.

In U.S. Pat. No. 5,380,299 a stent is provided with a coating of a thrombolytic compound and optionally an outer layer of an anti thrombotic compound. The stent may be precoated with a "primer" such as a cellulose ester or nitrate.

Other drug containing stents and stent coatings are described by Topol and Serruys in Circulation (1998) 98:1802-1820.

McNair et al, in Proceedings of the International Symposium on Controlled Release Bioactive Materials (1995) 338-339 describe in vitro investigations of release of three model drugs, caffeine, dicloxacillin and vitamin B12, from hydrogel polymers having pendant phosphorylcholine groups. Alteration of the hydrophilic hydrophobic ratio of the (hydrophilic) phosphorylcholine monomer 2-methacryloyloxyethyl phosphorylcholine, (HEMA-PC) and a hydrophobic comonomer and crosslinking of the polymer allows preparation of polymers having water contents when swollen in the range 45 to 70 wt %. Crosslinking is achieved by incorporating a reactive monomer 3-chloro-2-hydroxypropylmethacrylate. The tests are carried out on membranes swollen in aqueous drug solutions at 37° C. The release rates of the model drugs are influenced by the molecular size, solute partitioning and degree of swelling of the polymer. Dicloxacillin is found to have a higher half life for release than its molecular size would indicate, and the release profile did not appear to be Fickian.

McNair et al, in Medical Device Technology, Dec. 1996, 16-22, describe three series of experiments. In one, polymers formed of HEMA-PC and lauryl methacrylate crosslinked after coating by unspecified means are cocoated with drugs onto stents. Release rates of dexamethazone from the stent, apparently into an aqueous surrounding environment, was determined. Drug release from cast membranes, as model coatings, showed that the release rate obeyed Fickian diffusion principles, for hydrophilic solutes. In the third series of tests, a non-crosslinked polymer coating, free of drug, coated on a stent, had a significant decrease in platelet adhesion when coated on a stent used in an ex-vivo arteriovenous shunt experiment. The stent coating method was not described in detail.

Stratford et al in "Novel phosphorylcholine based hydrogel polymers:developments in medical device coatings" describe polymers formed from 2-methacryoyloxyethyl phosphorylcholine, a higher alkyl methacrylate, hydroxypropylmethacrylate and a methacrylate ester comonomer having a reactive pendant group. These PC polymers were investigated to determine the feasibility of delivering drugs and model drugs. Results are shown for caffeine, dicloxacillin, vitamin B12, rhodamine and dipyridamole. The device on which the drug is coated is a guide-wire that is, it is not an implant.

In our earlier application, WO-A-0004999, published after the priority date of the present application, we describe an apparatus suitable for coating tubular devices such as stents, which allows control of the relative thicknesses of the coatings on interior and exterior surfaces of the tubular substrate. It is suggested that the interior wall of a stent may be provided with a coating having a thickness in the range 5 to 200 nm, whilst the exterior surface may have a thicker coating, in the range 500 to 1500 nm. No specific examples of coating polymers are mentioned.

In EP-A-0623354, solutions of drug and polymer in a solvent were used to coat Wiktor type tantalum wire stents expanded on a 3.5 mm angioplasty balloon. The coating weights per stent were in the range 0.6 to 1.5 mg. Coating was either by dipping the stent in the solution, or by spraying the stent from an airbrush. In each case coating involved multiple coating steps. The drug was for delivery to the vessel wall.

In WO-A-92/11896, a method of delivering drug to the wall of a blood vessel from a hydrogel polymer on the outside of a balloon catheter is described. The drug is incorporated into the hydrogel which is compressed against the wall of the lumen upon expansion in the target vessel. In WO-A-98/11828, a stent is provided with a coating of a hydrogel, which may contain a drug, by transfer from the outer surface of the delivery balloon during the delivery procedure. In this case, drug will be delivered from the hydrogel on the interior wall of the stent, into the circulation. Another tubular implant for delivery of drug into the circulation, and which is to be implanted in a blood vessel is described in U.S. Pat. No. 5,735,897. In this device, drug is intended to permeate into the lumen and not through the exterior wall of the stent.

In WO-A-9421308, polyurethane coated on a stent is used as a drug delivery matrix. The stent is precoated with polyurethane which is subsequently immersed in a solution of drug in a solvent which swells the polyurethane. The polyurethane coating is at least 20 μm thick, for instance in the range 25 to 5000 μm. The level of drug in tissue adjacent to the stent as compared to drug in the system following stent delivery indicated higher levels in adjacent tissues than in the circulation, for lipophilic drugs, forskolin and etretinate. The method by which the stent is coated with polyurethane is not described in detail.

In a new process according to the invention, a sterile coated implant comprising a biostable implant and a coating comprising a polymer matrix is swollen in a pharmaceutical solution comprising a pharmaceutical active in solution in a solvent which swells the coating, the swelling being carried out at a temperature and for a time to allow swelling to an extent in the range 25 to 95% of the equilibrium swelling at 37° C. in the solution, and the coated implant is dried by solvent evaporation to remove 10 to 100% of total solvent, to produce a pharmaceutical active loaded implant, wherein the polymer of the matrix has pendant zwitterionic groups.

FIG. 1 represents Fractional Release versus SQRT (square root of time) for Example 3.

FIG. 2 represents Fractional Release versus SQRT for Example 4.

Figure 3:
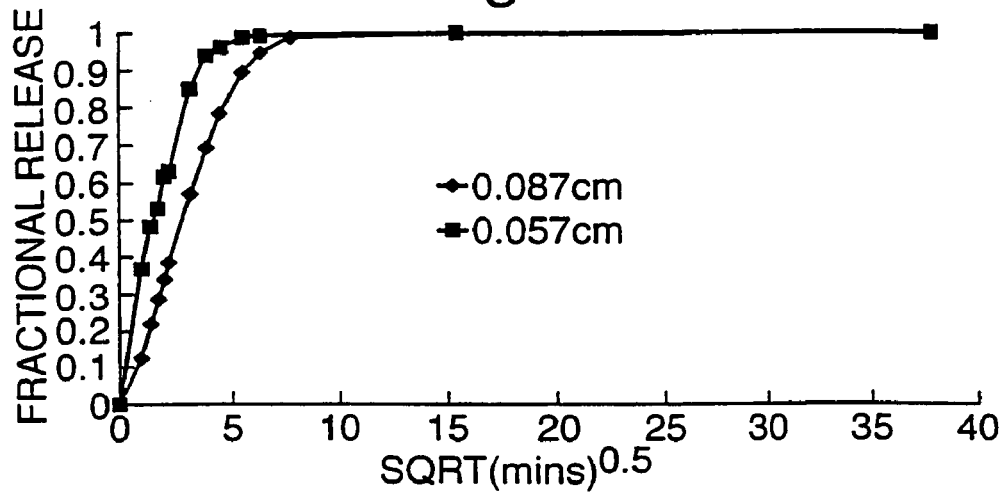
FIG. 3 represents Fractional Release versus SQRT for Example 5.

The polymer coated implant used in the swelling step should be sterile, such as generally provided ready to be used by a surgeon. The swelling step may be carried out immediately prior to a surgical operation in which the product implant is implanted into a patient in whom local release of the pharmaceutical active is desired. The sterile implant used in the swelling step may be produced in a preliminary process involving a step of coating the biostable implant with a coating composition containing the polymer, or a precursor therefore, curing the coating to form the polymer matrix and then sterilising the polymer coated implant.

The polymer matrix on the implant must be insoluble in the swelling solution. Preferably it is also water-insoluble. The polymer is generally substantially non-biodegradable (non-resorbable), in an environment to which implants are subjected, that is in the body. The polymer matrix should, for example, be stable in that environment, should not degrade significantly over a period of at least 2 days, preferably at least 2 weeks for instance a month or more. Although the polymer may be substantially non-crosslinked, such as formed from monomers including surface-substantive groups for stable surface binding on the implant, optimum stability is achieved where the polymer matrix is covalently crosslinked and/or covalently bound to the implant surface. Preferably the polymer is covalently crosslinked.

A crosslinked polymer matrix coating may be provided on an implant by polymerisation in situ of monomers including crosslinking monomer which forms crosslinks during the polymerisation reaction. Where the polymerisation is a condensation process, tri- and higher-functional monomers are used to achieve branching and crosslinking. Where, as is preferred, the monomers are ethylenically unsaturated and polymerisable by free radical initiated polymerisation, a crosslinking monomer is a di-, tri- or higher-functional ethylenically unsaturated monomer. The coating is thus formed by application of a liquid polymerisation mixture onto the implant surface followed by initiation of polymerisation under suitable radical generating conditions.

For optimum control of the polymer product, however, it is preferred for a crosslinkable polymer to be presynthesised, used to coat the implant and, after coating, subjected to conditions under which crosslinking takes place. The crosslinkable polymers are generally formed from monomers including pendant reactive groups which do not react under the polymerisation conditions, but only later under the subsequent crosslinking conditions. Such conditions may involve application of heat, for instance raising the coating to a temperature in the range 40 to 70° C., in the presence of moisture, for instance at at least 50% relative humidity.

Most preferably the polymer is formed from ethylenically unsaturated monomers including a zwitterionic monomer. Preferably the ethylenically unsaturated monomers include a surface binding monomer, usually a hydrophobic comonomer. For forming a crosslinkable polymer, the ethylenically unsaturated monomers preferably include one or more reactive monomer having a pendant reactive group(s) capable of forming intermolecular crosslinks.

Preferably the zwitterionic monomer has the general formula I:

$$YBX \qquad I$$

wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from

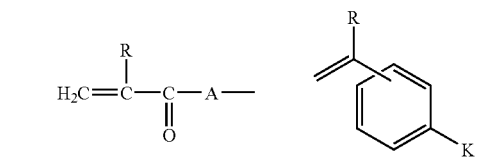

$CH_2{=}C(R)CH_2O{-}$, $CH_2{=}C(R)CH_2OC(O){-}$, $CH_2{=}C(R)OC(O){-}$, $CH_2{=}C(R)O{-}$, $CH_2{=}C(R)CH_2OC(O)N(R^1){-}$, $R^2OOCCR{=}CRC(O)O{-}$, $RCH{=}CHC(O)O{-}$, $RCH{=}C(COOR^2)CH_2C(O)O{-}$,

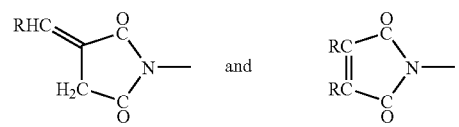

wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1-4}$ alkyl group;

A is —O— or —$NR^1$—;

K is a group —$(CH_2)POC(O)$—, —$(CH_2)_pC(O)O$—, —$(CH_2)POC(O)O$—, —$(CH_2)_pNR^3$—, —$(CH_2)_pNR^3C(O)$—, —$(CH_2)_pPC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, or, optionally in combination with B, a valence bond p is from 1 to 12; and $R^3$ is hydrogen or a $C_1$-$C_4$ alkyl group.

In group X, the atom bearing the cationic charge and the atom bearing the anionic charge are generally separated by 2 to 12 atoms, preferably 2 to 8 atoms, more preferably 3 to 6 atoms, generally including at least 2 carbon atoms.

Preferably the cationic group in zwitterionic group X is an amine group, preferably a tertiary amine or, more preferably, a quaternary ammonium group. The anionic group in X may be a carboxylate, sulphate, sulphonate, phosphonate, or more preferably, phosphate group. Preferably the zwitterionic group has a single monovalently charged anionic moiety and a single monovalently charged cationic moiety. A phosphate group is preferably in the form of a diester.

Preferably, in a pendant group X, the anion is closer to the polymer backbone than the cation.

Alternatively group X may be a betaine group (ie in which the cation is closer to the backbone), for instance a sulpho-, carboxy- or phospho-betaine. A betaine group should have no overall charge and is preferably therefore a carboxy- or sulpho-betaine. If it is a phosphobetaine the phosphate terminal group must be a diester, i.e., be esterified with an alcohol. Such groups may be represented by the general formula II

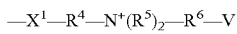
$$—X^1—R^4—N^+(R^5)_2—R^6—V \qquad II$$

in which $X^1$ is a valence bond, —O—, —S— or —NH—, preferably —O—;

V is a carboxylate, sulphonate or phosphate (diester-monovalently charged) anion;

$R^4$ is a valence bond (together with $X^1$) or alkylene —C(O)alkylene- or —C(O)NHalkylene preferably alkylene and preferably containing from 1 to 6 carbon atoms in the alkylene chain;

the groups $R^5$ are the same or different and each is hydrogen or alkyl of 1 to 4 carbon atoms or the groups $R^5$ together with the nitrogen to which they are attached form a heterocyclic ring of 5 to 7 atoms; and $R^6$ is alkylene of 1 to 20, preferably 1 to 10, more preferably 1 to 6 carbon atoms.

One preferred sulphobetaine monomer has the formula II

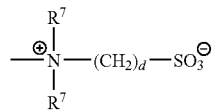

where the groups $R^7$ are the same or different and each is hydrogen or $C_{1-4}$ alkyl and d is from 2 to 4.

Preferably the groups $R^7$ are the same. It is also preferable that at least one of the groups $R^7$ is methyl, and more preferable that the groups $R^7$ are both methyl.

Preferably d is 2 or 3, more preferably 3.

Alternatively the group X may be an amino acid moiety in which the alpha carbon atom (to which an amine group and the carboxylic acid group are attached) is joined through a linker group to the backbone of polymer A. Such groups may be represented by the general formula IV

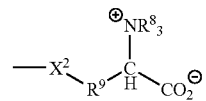

in which $X^2$ is a valence bond, —O—, —S— or —NH—, preferably —O—, $R^9$ is a valence bond (optionally together with $X^2$) or alkylene, —C(O)alkylene- or —C(O)NHalkylene, preferably alkylene and preferably containing from 1 to 6 carbon atoms; and the groups $R^8$ are the same or different and each is hydrogen or alkyl of 1 to 4 carbon atoms, preferably methyl, or two of the groups $R^8$, together with the nitrogen to which they are attached, form a heterocyclic ring of from 5 to 7 atoms, or the three group $R^8$ together with the nitrogen atom to which they are attached form a fused ring structure containing from 5 to 7 atoms in each ring.

X is preferably of formula V

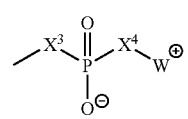

in which the moieties $X^3$ and $X^4$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group.

Preferably W contains as cationic group an ammonium group, more preferably a quaternary ammonium group.

The group $W^+$ may for example be a group of formula —$W^1$—$N^+R^{10}_3$, —$W^1$—$P^+R^{11}_3$, —$W^1$—$S^+R^{11}_2$ or —$W^1$-$Het^+$ in which:

$W^1$ is alkanediyl of 1 or more, preferably 2-6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups RIO are the same or different and each is hydrogen or alkyl of 1 to 4 carbon atoms, preferably methyl, or aryl, such as phenyl or two of the groups $R^{10}$ together with the nitrogen atom to which they are attached form a heterocyclic ring containing from 5 to 7 atoms or the three groups $R^{10}$ together with the nitrogen atom to which they are attached form a fused ring structure containing from 5 to 7 atoms in each ring, and optionally one or more of the groups $R^{10}$ is substituted by a hydrophilic functional group, and the groups $R^{11}$ are the same or different and each is $R^{10}$ or a group $OR^{10}$, where $R^{10}$ is as defined above; or Het is an aromatic nitrogen-, phosphorus- or sulphur-, preferably nitrogen-, containing ring, for example pyridine.

Preferably $W^1$ is a straight-chain alkanediyl group, most preferably ethane-1,2-diyl.

Preferred groups X of the formula V are groups of formula VI:

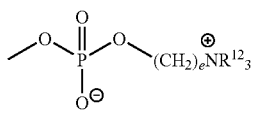

where the groups $R^{12}$ are the same or different and each is hydrogen or $C_{1-4}$ alkyl, and e is from 1 to 4.

Preferably the groups $R^{12}$ are the same. It is also preferable that at least one of the groups $R^{12}$ is methyl, and more preferable that the groups $R^{12}$ are all methyl.

Preferably e is 2 or 3, more preferably 2.

Alternatively the ammonium phosphate ester group VIII may be replaced by a glycerol derivative of the formula VB, VC or VD defined in our earlier publication no WO-A-93/01221.

Preferably the surface binding comonomer has the general formula VII $$Y^1R^{13} \qquad\qquad VII$$

wherein $Y^1$ is selected from

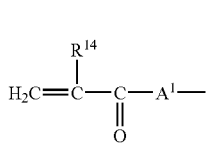 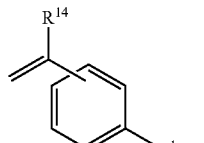

$CH_2$=$C(R^{14})CH_2$—O—, $\quad CH_2$=$C(R^{14})CH_2OC(O)$—,
$CH_2$=$C(R^{14})OC(O)$—, $CH_2$=$C(R^{14})O$—, $CH_2$=$C(R^{14})$
$CH_2OC(O)N(R^{15})$—, $\quad R^{16}OOCCR^{14}$=$CR^{14}C(O)O$—,
$R^{14}CH$=$CHC(O)O$—, $\quad R^{14}CH$=$C(COOR^{16})CH_2C(O)$—
O—,

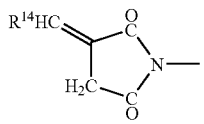 and 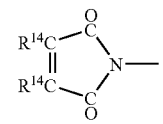

wherein:
$R^{14}$ is hydrogen or a $C_1$-$C_4$ alkyl group;
$R^{15}$ is hydrogen or a $C_1$-$C_4$ alkyl group or $R^{15}$ is $R^{13}$;
$R^{16}$ is hydrogen or a $C_{1-4}$ alkyl group;
$A^1$ is —O— or —$NR^{15}$—; and
$K^1$ is a group —$(CH_2)_qOC(O)$—, —$(CH_2)_qC(O)O$—, $(CH_2)_qOC(O)O$—, —$(CH_2)_qNR^{17}$—, —$(CH_2)_qNR^{17}C$(O)—, —$(CH_2)_qC(O)NR^{17}$—, —$(CH_2)_qNR^{17}C(O)O$—, —$(CH_2)_qOC(O)NR^{17}$—, —$(CH_2)_qNR^{17}C(O)NR^{17}$— (in which the groups $R^{17}$ are the same or different), —$(CH_2)_qO$—, —$(CH_2)_qSO_3$—, or a valence bond
p is from 1 to 12;
and $R^{17}$ is hydrogen or a $C_1$-$C_4$ alkyl group;
and $R^{13}$ is a surface binding group, selected from hydrophobic groups and ionic groups.

In the comonomer of the general formula VII, the group $R^{13}$ is preferably a hydrophobic group, preferably:

a) a straight or branched alkyl, alkoxyalkyl or oligoalkoxyalkyl chain containing 6 or more, preferably 6 to 24 carbon atoms, unsubstituted or substituted by one or more fluorine atoms optionally containing one or more carbon double or triple bonds; or b) a siloxane group —$(CR^{18}_2)_{qq}(SiR^{19}_2)(OSiR^{19}_2)_{pp}R^{19}$ in which each group $R^{18}$ is the same or different and is hydrogen or alkyl of 1 to 4 carbon atoms, or aralkyl, for example benzyl or phenethyl, each group $R^{19}$ is alkyl of 1 to 4 carbon atoms, qq is from 1 to 6 and pp is from 0 to 49

Most preferably $R^{13}$ is a straight alkyl having 8 to 18, preferably 12 to 16 carbon atoms.

The reactive monomer to which provides crosslinkability preferably has the general formula VIII $$Y^2B^2R^{20} \qquad\qquad VIII$$

wherein
$B^2$ is a straight or branched alkylene, oxaalkylene or oligo-oxaalkylene chain optionally containing one or more fluorine atoms up to and including perfluorinated chains, or $B^2$ is a valence bond;
$Y^2$ is an ethylenically unsaturated polymerisable group selected from

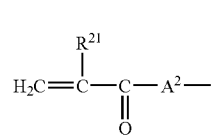 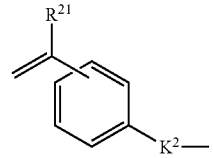

$CH_2$=$C(R^{21})CH_2$—O—, $\quad CH_2$=$C(R^{21})CH_2OC(O)$—,
$CH_2$=$C(R^{21})OC(O)$—, $CH_2$=$C(R^{21})O$—, $CH_2$=$C(R^{21})$
$CH_2OC(O)N(R^{22})$—, $\quad R^{23}OOCCR^{21}$=$CR^{21}C(O)$—,
$R^{21}H$=$CHC(O)O$—, $R^{21}H$=$C(COOR^{23})CH_2C(O)O$—

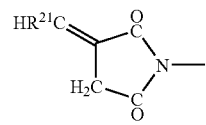 and 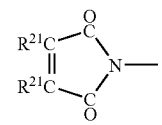

where
$R^{21}$ is hydrogen or $C_1$-$C_4$ alkyl;
$R^{23}$ is hydrogen, or a $C_{1-4}$-alkyl group;
$A^2$ is —O— or —$NR^{22}$—;
$R^{22}$ is hydrogen or a $C_1$-$C_4$ alkyl group or $R^{22}$ is a group $B^2R^{20}$;
$K^2$ is a group —$(CH_2)_kOC(O)$—, —$(CH)_kC(O)O$—, —$(CH_2)_kOC(O)O$—, —$(CH_2)_kNR^{22}$—, —$(CH_2)_kNR^{22}C$(O)—, —$(CH_2)_kOC(O)O$—, —$(CH_2)_kNR^{22}$—, —$(CH_2)_k$ $NR^{22}C(O)$—, —$(CH_2)_kC(O)NR^{22}$—, —$(CH_2)_kNR^{22}C(O)$ O—, —$(CH_2)_kOC(O)NR^{22}$—, —$(CH_2)_kNR^{22}C(O)NR^{22}$— (in which the groups $R^{22}$ are the same or different), —$(CH_2)_k$ O—, —$(CH_2)_kSO_3$—, a valence bond and k is from 1 to 12; and
$R^{20}$ is a cross-linkable group.

Group $R^{20}$ is selected so as to be reactive with itself or with a functional group in the polymer (eg in group $R^{13}$) or at a surface to be coated. The group $R^{20}$ is preferably a reactive group selected from the group consisting of ethylenically and acetylenically unsaturated group containing radicals; aldehyde groups; silane and siloxane groups containing one or more substituents selected from halogen atoms and $C_{1-4}$-alkoxy groups; hydroxyl; amino; carboxyl; epoxy; —CHOHCH$_2$Hal (in which Hal is selected from chlorine, bromine and iodine atoms); succinimido; tosylate; triflate; imidazole carbonyl amino; optionally substituted triazine groups; acetoxy; mesylate; carbonyl di(cyclo)alkyl carbodiimidoyl; isocyanate, acetoacetoxy; and oximino. Most preferably R$^{20}$ comprises a silane group containing at least one, preferably three substituents selected from halogen atoms and $C_{1-4}$-alkoxy groups, preferably containing three methoxy groups.

Preferably each of the groups Y to Y$^2$ is represented by the same type of group, most preferably each being an acrylic type group, of the formula H$_2$C=C(R)C(O)-A, H$_2$C=C(R$^{14}$)C(O)A$^1$ or H$_2$C=C(R$^{21}$)C(O)-A$^2$, respectively. Preferably the groups R, R$^{14}$ and R$^{21}$ are all the same and are preferably H or, more preferably, CH$_3$. Preferably A, A$^1$ and A$^2$ are the same and are most preferably —O—. B and B$^2$ are preferably straight chain $C_{2-6}$-alkanediyl.

Preferably the ethylenically unsaturated comonomers comprise diluent comonomers which may be used to give the polymer desired physical and mechanical properties. Particular examples of diluent comonomers include alkyl(alk)acrylate preferably containing 1 to 24 carbon atoms in the alkyl group of the ester moiety, such as methyl(alk)acrylate or dodecyl methacrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl(alk)acrylate; an alkyl (alk)acrylamide preferably containing 1 to 4 carbon atoms in the alkyl group of the amide moiety; a hydroxyalkyl(alk)acrylate preferably containing from 1 to 4 carbon atoms in the hydroxyalkyl moiety, e.g. a 2-hydroxyethyl (alk)acrylate glycerylmonomethacrylate or polyethyleneglycol monomethacrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Diluent comonomers include methacryloyl glucose and sorbitol methacrylate.

Further diluents which may be mentioned specifically include polymerisable alkenes, preferably of 2-4 carbon atoms, eg. ethylene, dienes such as butadiene, ethylenically unsaturated dibasic acid anhydrides such as maleic anhydride and cyano-substituted alkenes, such as acrylonitrile.

Particularly preferred diluent monomers are nonionic monomers, most preferably alkyl(alk)acrylates or hydroxyalkyl(alk)acrylates.

It is particularly desirable to include hydroxyalkyl(alk) acrylates in combination with reactive comonomers which contain reactive silyl moieties including one or more halogen or alkoxy substituent. The hydroxyalkyl group containing monomer may be considered a reactive monomer although it also acts as a diluent. Such reactive silyl groups are reactive with hydroxy groups to provide crosslinking of the polymer after coating, for instance.

A particularly preferred combination of reactive monomers is ω(trialkoxysilyl)alkyl(meth)acrylate and an ω-hydroxyalkyl(meth)acrylate.

Preferably the zwitterionic monomer is used in the monomer mixture in a molar proportion of at least 1%, preferably less than 75%, more preferably in the range 5 to 50%, most preferably 10-33%. The surface binding comonomer is generally used in molar proportion of at least 2%, preferably at least 5% or at least 10%, more preferably in the range 15 to 99%. Where the surface binding monomer comprises hydrophobic physisorbable groups, it is preferably present in a molar amount in the range 30 to 99%. Where the polymer is not covalently bonded to the substrate or cross-linked, the amount of hydrophobic surface binding monomer is preferably in the range 50 to 95%, more preferably 60 to 90%. The cross-linkable monomer is preferably used in a molar amount in the range 2 to 33%, preferably 3 to 20%, more preferably 5 to 10% by mole.

The zwitterionic polymer can be represented by the general formula IX:

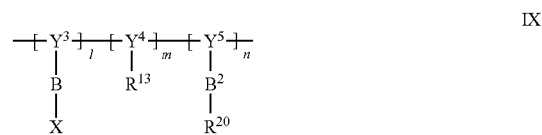

IX in which l is 1 to 75, m is 0 to 99, n is 0 to 33 and m+n is 25 to 99, Y$^3$ to Y$^5$ are the groups derived from Y to Y$^2$, respectively, of the radical initiated addition polymerisation of the ethylenic group in Y to Y$^2$, and B and X are as defined for the general formula I,
R$^{13}$ is as defined for the general formula VII, and
B$^2$ and R$^{20}$ are as defined for the general formula VIII.

In the preferred zwitterionic polymer in which Y, Y$^1$ and Y$^2$ are each acrylic groups the polymer has the general formula X

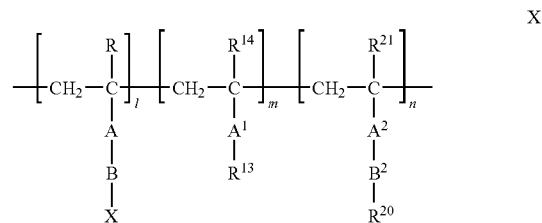

X in which B, X, R and A are as defined for the compound of the general formula I, R$^{14}$, A$^1$ and R$^{13}$ are as defined for the general formula VII, R$^{21}$, D$^2$, B$^2$ and R$^{20}$ are as defined for the general formula VIII and l, m and n are as defined for the general formula IX The polymerisation is carried out using suitable conditions as known in the art. Thus the polymerisation involves radical initiation, using thermal or redox initiators which generate free radicals and/or actinic (e.g. u.v or gamma) radiation, optionally in combination with photoinitiators and/or catalysts. The initiator is preferably used in an amount in the range 0.05 to 5% by weight based on the weight of monomer preferably an amount in the range 0.1 to 3%, most preferably in the range 0.5 to 2%. The level of initiator is generally higher where the monomer includes reactive monomer and the polymer is cross-linkable, eg 1 to 20%.

The molecular weight of the polymer (as coated, where the polymer is cross-linkable) is in the range $1 \times 10^4$ to $1 \times 10^6$, preferably in the range $5 \times 10^4$ to $5 \times 10^5$ D.

The monomer mixture and the monomer mixture may include a non-polymerisable diluent, for instance a polymerisation solvent. Such a solvent may provide solubility and miscibility of the monomers. The solvent may be aqueous or non-aqueous. The polymer may be recovered by precipitation from the polymerisation mixture using a precipitating solvent, or recovery may involve removal of any non polymerisable diluent by evaporation, for instance.

The implant used in the invention is generally for substantially permanent implantation. It may be formed of a polymeric, for instance a synthetic polymeric, material or, preferably, is formed of metal. The device may be a catheter, a graft or a stent graft, but is preferably a stent, generally a permanent stent. The stent is suitable for use for insertion into any body lumen, such as of the urinary tract, or GI tract. Preferably it is suitable for implantation into a blood vessel, especially a coronary blood vessel.

According to a further aspect of the invention an implant selected from a graft, a stent and a stent-graft having a polymer matrix coating on its inner and outer surfaces, is loaded with a pharmaceutical active by swelling the polymer matrix in a solution of the active, and is characterised further in that the polymer of the matrix is a cross-linked polymer formed from ethylenically unsaturated monomer including a) a zwitterionic monomer of the general formula I $$YBX \qquad\qquad I$$

wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from

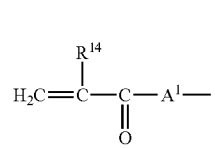
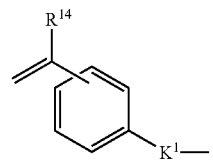

$CH_2\!=\!C(R)CH_2O\!-\!$, $CH_2\!=\!C(R)CH_2OC(O)\!-\!$, $CH_2\!=\!C(R)OC(O)\!-\!$, $CH_2\!=\!C(R)O\!-\!$, $CH_2\!=\!C(R)CH_2OC(O)N(R^1)\!-\!$, $R^2OOCCR\!=\!CRC(O)O\!-\!$, $RCH\!=\!CHC(O)O\!-\!$, $RCH\!=\!C(COOR^2)CH_2C(O)O\!-\!$,

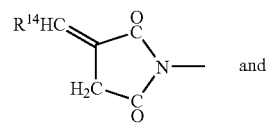 and 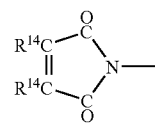

wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1\text{-}4}$ alkyl group;

A is —O— or —NR$^1$—;

K is a group $-(CH_2)_pOC(O)-$, $-(CH_2)_pC(O)O-$, $-(CH_2)_pOC(O)O-$, $-(CH_2)_pNR^3-$, $-(CH_2)_pNR^3C(O)-$, $-(CH_2)_pC(O)NR^3-$, $-(CH_2)_pNR^3C(O)O-$, $-(CH_2)_pOC(O)NR^3-$, $-(CH_2)_pNR^3C(O)NR^3-$ (in which the groups $R^3$ are the same or different), $-(CH_2)_pO-$, $-(CH_2)_pSO_3-$, or, optionally in combination with B, a valence bond p is from 1 to 12; and $R^3$ is hydrogen or a $C_1$-$C_4$ alkyl group;

b) a surface binding monomer of the general formula VII $$Y^1R^{13} \qquad\qquad VII$$

wherein $Y^1$ is selected from

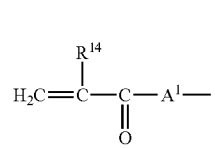
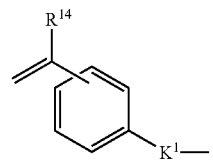

$CH_2\!=\!C(R^{14})CH_2O\!-\!$, $CH_2\!=\!C(R^{14})CH_2OC(O)\!-\!$, $CH_2\!=\!C(R^{14})OC(O)\!-\!$, $CH_2\!=\!C(R^{14})O\!-\!$, $CH_2\!=\!C(R^{14})CH_2OC(O)N(R^{15})\!-\!$, $R^{16}OOCCR^{14}\!=\!CR^{14}C(O)O\!-\!$, $R^{14}CH\!=\!CHC(O)O\!-\!$, $R^{14}CH\!=\!C(COOR^{16})CH_2C(O)O\!-\!$,

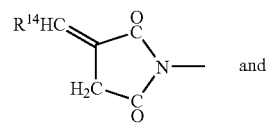 and 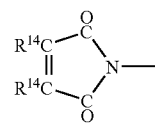

wherein:

$R^{14}$ is hydrogen or a $C_1$-$C_4$ alkyl group;

$R^{15}$ is hydrogen or a $C_1$-$C_4$ alkyl group or $R^{15}$ is $R^{13}$;

$R^{16}$ is hydrogen or a $C_{1\text{-}4}$ alkyl group;

$A^1$ is —O— or —NR$^{15}$—; and $K^1$ is a group $-(CH_2)_qOC(O)-$, $-(CH_2)_qC(O)O-$, $-(CH_2)_qOC(O)O-$, $-(CH_2)_qNR^{17}-$, $-(CH_2)_qNR^{17}C(O)-$, $-(CH_2)_qC(O)NR^{17}-$, $-(CH_2)_qNR^{17}C(O)O-$, $-(CH_2)_qOC(O)NR^{17}-$, $-(CH_2)_qNR^{17}C(O)NR^{17}-$ (in which the groups $R^{17}$ are the same or different), $-(CH_2)_qO-$, $-(CH_2)_qSO_3-$, or a valence bond p is from 1 to 12;

and $R^{17}$ is hydrogen or a $C_1$-$C_4$ alkyl group;

and $R^{13}$ is a surface binding group, selected from hydrophobic groups and ionic groups; and c) a reactive monomer of the general formula VIII $$Y^2B^2R^{20} \qquad\qquad VIII$$

wherein $B^2$ is a straight or branched alkylene, oxaalkylene or oligo-oxaalkylene chain optionally containing one or more fluorine atoms up to and including perfluorinated chains, or $B^2$ is a valence bond;

$Y^2$ is an ethylenically unsaturated polymerisable group selected from

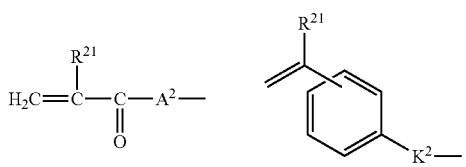

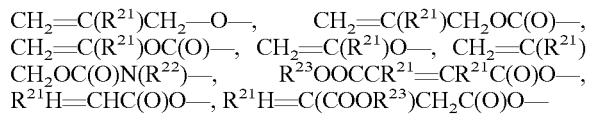

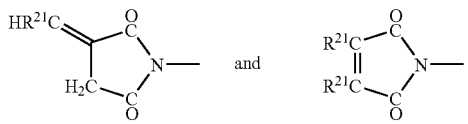

where
R$^{21}$ is hydrogen or C$_1$-C$_4$ alkyl;
R$^{23}$ is hydrogen, or a C$_{1-4}$-alkyl group;
A$^2$ is —O— or —NR$^{22}$—;
R$^{22}$ is hydrogen or a C$_1$-C$_4$ alkyl group or R$^{22}$ is a group B$^2$R$^{20}$;
K$^2$ is a group —(CH$_2$)$_k$OC(O)—, —(CH)$_k$C(O)O—, —(CH$_2$)$_k$OC(O)O—, —(CH$_2$)$_k$NR$^{22}$—, —(CH$_2$)$_k$NR$^{22}$C(O)—, —(CH$_2$)$_k$OC(O)O—, —(CH$_2$)$_k$NR$^{22}$—, —(CH$_2$)$_k$NR$^{22}$C(O)—, —(CH$_2$)$_k$C(O)NR$^{22}$—, —(CH$_2$)$_k$NR$^{22}$C(O)O—, —(CH$_2$)$_k$OC(O)NR$^{22}$—, —(CH$_2$)$_k$NR$^{22}$C(O)NR$^{22}$— (in which the groups R$^{22}$ are the same or different), —(CH$_2$)$_k$O—, —(CH$_2$)$_k$SO$_3$—, a valence bond and k is from 1 to 12; and
R$^{20}$ is a silyl group having three alkoxy substituents.

Preferably the polymer also comprises a further reactive monomer of the formula VIII, in which R$^{20}$ is a hydroxyl group.

Such polymers are cross-linked by heating. The polymers preferably have the monomer ratios mentioned above, and are synthesised and coated using the above described techniques.

The polymer matrix coatings are stable to conditions used during sterilisation techniques. For instance sterilisation may be carried out by ethylene oxide or gamma irradiation. Following sterilisation the product device is usually packaged for storage, transportation to a hospital or surgery etc. It is an advantage of the present invention that a stent provided with a polymer matrix coating is suitable for use as a delivery device for a range of pharmaceutical actives. The choice of pharmaceutical active may thus lie with the medical practitioner, determined upon the basis of his diagnosis.

The step of swelling the coating is carried out by dipping the polymer matrix coated device into the solution, by spraying the device with the solution or a combination of dipping and spraying. The dipping and spraying may be carried out intermittently, for instance with drying phases between the immersion or spraying phases.

It is particularly preferred that the polymer matrix coated on the outer surface of the implant has a coating thickness 1.5 to 50 times that of the polymer matrix on the interior wall surface, more preferably at least 2 times that of the thickness of the coating on the interior wall surface.

A coating on a stent can be considered a monolith for the purposes of calculating the release of a drug. Release is governed by equation 1 (Baker, R W et al in "Controlled Release of Biologically Active Agents, 15, Tanquary A C and Lacey R E (Eds) Plenum Press, NY (1973)):

$$\frac{M_t}{M_\infty} = 4\left\{\frac{Dt}{\pi l^2}\right\}^{0.5} \text{ where } 0 \leq M_t/M_\infty < 0. \quad \text{Equation 1}$$

in which M$_t$ is the mass of drug release after time t, m is the total amount of drug which can be released, l is the thickness of the coating and D is the coefficient of diffusion of the drug in the polymer matrix.

It can be seen that the half life varies with the square of the thickness. In the present invention the swollen thickness of the polymer matrix/pharmaceutical active coating in the product device is in the range 100 nm to 1000 µm, most preferably in the range 200 nm to 100 µm. The thickness of the polymer matrix before swelling is preferably in the range 20 nm to 1 mm, preferably 50 nm to 500 µm, for instance more than 500 nm at least on the exterior surface, and less than 5 µm.

The polymer/pharmaceutical active combination is selected so as to give suitable release rates, as desired. Furthermore, the release half life, and consequently period over which the pharmaceutical active will be released, may be controlled by selection of a suitable coating thickness. The diffusion coefficient can be calculated by experiment, for instance following the techniques used in the examples below. The suitable thickness can be calculated from the desired total loading levels and rate of delivery required, from equation 1 above.

The solvent in the pharmaceutical active containing solution used to load the polymer matrix coating is selected for its compatibility with the polymer and with the pharmaceutical active. Thus it must be a solvent for the pharmaceutical active and the solution must swell the polymer matrix at a convenient rate.

The period over which the polymer matrix coating is swollen in the pharmaceutical active containing solution is preferably no more 24 hours, most preferably less than 12 hours, for instance less than 3 hours, most preferably less than 30 minutes. The period is usually more than 30 s, usually more than 1 minute, for instance 5 minutes or more.

Swelling is conducted at ambient temperature, for instance around 20 to 25° C., or at raised temperature, for instance body temperature, 37° C. The polymers generally swell faster at higher temperatures, for instance at 37° C. The rate of swelling of the polymer matrix depends also on the diffusion coefficient of the solvent in the polymer, which in turn depends upon the nature of the polymer including its level of crosslinking. The thickness of the coating also affects the period over which the swelling step should take place. The pharmaceutical active, the solute in the solution, may also affect the rate of swelling of the polymer in the solution. These parameters can be determined and optimised empirically.

In the invention it is preferred that the pharmaceutical-loaded coating be continuous over the coated surface. Preferably it should be of substantially uniform thickness on the or each surface coated. Where the product is a stent, or a graft, it is particularly preferred for the coating to be on both sides of the device, but that it be of different thickness on the inside to the outside of the device. It is preferred that a larger reservoir of drug be provided on the outer surface where it is released directly into the tissue with which it is in contact during use. Since systemic delivery is generally to be minimised, at least in the long term, the coating on the inner surface is preferably thin.

The ratio of thicknesses between the exterior and interior wall surfaces of a stent or a graft is generally (at least 1.5):1, preferably (at least 2):1 and often higher than this, for instance (up to 10):1 or more, eg (up to 50):1. It is desirable that the interior wall surface be provided with a coating of polymer matrix to provide biocompatibility, especially non-thrombogenicity.

A thicker coating of the polymeric matrix may be provided on the outer surface of a stent or a graft by selection of a suitable coating technique. For a stent, which has openings in its tubular wall, coating of optimum uniformity is achieved by a dipping process. To achieve a lower coating thickness on the inner surface in the product, liquid coating may be removed from the inner surface prior to drying, for instance by directing a flow of fluid through the inner lumen, generally of gas, for instance air. Preferably coating is carried out as described in WO-A-0004999, to provide a thinner coating on the interior wall as compared to the exterior wall.

The choice of the solvent is governed by the rate of swelling of the polymer matrix, the solubility characteristics of the pharmaceutical active as well as the pharmaceutical acceptability. The solvent is suitably, for instance, an alcohol, including a glycol, water or mixtures thereof. An alcohol is preferably a lower alkanol, for instance ethanol or isopropanol. Most preferably the solvent is aqueous.

The pharmaceutical active solution may contain ingredients such as salts, buffers, pH modifying agents, dyes, etc.

Equilibrium swelling of the polymer matrix coated implant may be determined by monitoring the rate of progress of swelling after contact of the implant with the pharmaceutical active solution, for instance by removing the partially swollen device, drying off residual solvent and monitoring the gain in weight. The equilibrium swelling may, alternatively, be calculated from a knowledge of the swellability of the polymer matrix itself in the respective solution at 37° C., and the thickness of the coating on the implant, using formula 1 above. Whilst the equilibrium swelling may be affected by the nature of the pharmaceutical active, it is generally substantially the same as the equilibrium swelling in the solvent excluding the drug, especially where the drug is uncharged. The equilibrium swelling can thus be determined or calculated from the swelling in the solvent itself, generally including any salt or buffer.

We believe that the provision of a stent having a coating comprising polymer and elutable pharmaceutical active on interior and exterior walls in which the thickness of the polymer coating on the exterior wall of the stent is at least 1.5 times the thickness of the coating on the interior wall, is novel and forms a further aspect of the invention. In this aspect, the stent is for temporary or, more preferably, permanent implantation into a body lumen, and is formed of an impermeable generally tubular body having an interior and an exterior wall, the impermeable material of the body being substantially entirely coated with a biocompatible coating. The is preferably formed of metal, and may be formed of wire, for instance by braiding or other shaping means into a tube shape. Preferably the stent is formed from a tube by cutting or etching through the thickness of the tube to form openings.

In this aspect of the invention, the pharmaceutical active is a compound which is required to be delivered to the vessel wall in which the stent is to be implanted, but is preferred to be released into the circulation at very low rates. The material of the stent, being metal, is impermeable to pharmaceutical actives. Accordingly, by providing a thicker polymer matrix from which drug is delivered from the exterior wall as compared to the thickness of the coating on the interior wall, the rate of delivery of drug from the exterior wall into the vessel after implantation will be optimised, whilst minimising the extent of delivery of the pharmaceutical active into the circulation.

In this aspect of the invention, the polymer is present on the stent at a thickness such that the polymer thickness under physiological in use conditions (when swollen with physiological saline at 37° C.) is in the range 100 nm to 100 μm on the exterior wall of the stent. The respective thickness on the interior wall is lower, and should preferably be less than 5 μm. The ratio of thicknesses is preferably as described above.

In this aspect of the invention, the polymer is a material which, when in contact with aqueous fluids, is permeable to the pharmaceutical active. The polymer should preferably be a water-swellable material.

The polymer may be any biocompatible polymer which has been used to provide biocompatible coatings on stents or other implants. Preferably the polymer is biostable and hence water-insoluble, for instance biodegradable or bioerodable polymers. Preferably the polymer is water-swellable, since the diffusion of solvents through hydrogels is controllable and such materials provide controlled release delivery systems. The polymer may, for instance, be a silicone hydrogel, a polyurethane, or polyethers, such as polyethylene glycol, polyamides, polyesters, such as hydroxy-butyric acid polymers and copolymers, poly(lactides) or polyacrylic polymers. Preferably the polymer is crosslinked zwitterionic polymer, most preferably a polymer of the type described above in connection with the first and second aspect of the invention.

In this aspect of the invention, the stent may be provided with pharmaceutical active preloaded into the polymer matrix, rather than being loaded immediately before by a surgeon. The polymer may be mixed with drug before coating on to the stent. Where the polymer in the product is cross-linked, the coating composition preferably contains cross-linkable polymer, which is cross-linked after coating, ie in the presence of the drug. We have found that low molecular weight actives, for instance having molecular weight up to about 1200 D, are released from such coatings, at approximately the same rate as the drug loaded in the preformed coating.

The polymer/pharmaceutical active coating is preferably in an unswollen state when supplied ready for use. The stent may be preloaded onto a delivery catheter, or may be loaded by the surgeon onto such catheter immediately before use. In either event, the stent may be delivered dry into the body passageway of a patient or, alternatively, may be wetted with saline or an aqueous solution of another pharmaceutical active.

Alternatively, the stent with loaded pharmaceutical active and differential polymer matrix thickness may be produced immediately before use by dipping a suitable polymer coated stent into a loading solution of a pharmaceutical active. In this case, the polymer coated stent may be pre-mounted on a delivery catheter or may be mounted onto such a device after loading of the pharmaceutical active. Preferably the loading is carried out as described above by swelling the polymer coated stent in a aqueous pharmaceutical active solution to swell at least partially the polymer coating, followed by optional drying prior to delivery into a patient.

The pharmaceutical active used in all aspects of the present invention is preferably selected from the following classes of drugs: anti-proliferatives, such as growth factor antagonists, migration inhibitors, somatostatin analogues, ACE-inhibitors, and lipid-lowering drugs; anti-coagulants, such as direct anti-coagulants which inhibit the clotting cascade, indirect anti-coagulants, which depress the synthesis of clotting factors, anti-platelet (aggregation) drugs, such as thromboxane A2 inhibitors or antagonists, adenosine inhibitors, glycoprotein receptor Iib/IIIa antagonists, thrombin inhibitors; vasodilators, including vasoconstriction antagonists, such as ACE inhibitors, angiotensin II receptor antagonists, serotonin receptor antagonists, and thromboxane A2 synthetase inhibitors, and other vasodilators; anti-inflammatories; cytotoxic agents, such as anti-neoplastic agents, alkylating agents, antimetabolites, mitotic inhibitors, and antibiotic antineoplastic agents; and radioactive agents or targets thereof, for local radiation therapy. The active is most preferably an anti-angiogenic compound, for instance an antithrombotic compound and/or an anti-proliferative agent. Suitable examples of pharmaceutical actives include dipyrimadole, angiopeptin, rapamycin, roxithromycin, etoposide, aspirin and dexamethasone.

The following examples illustrate the invention:

EXAMPLE 1

HEMA-PC-co-LM 1:2 Copolymer

A polymer was synthesised by copolymerising 1 part (mole) 2-methacryloyloxyethyl-2'-trimethylammoniumethyl phosphate inner salt with 2 parts dodecylmethacrylate, according to the technique of example 1 of WO-A-93/01221. The copolymer is subsequently used in the examples below.

EXAMPLE 2

Drug Delivery from HEMA-PC-co-LM 1:2 Copolymer

The implants tested were commercially available Johnson & Johnson Palmaz-Schatz stents. These were coated by dipping them in solutions containing 100 mg/ml of HEMA-PC-co-LM 1:2 produced in example 1.

Caffeine Loading

Initial stent loading was performed by swelling the coated stents in aqueous solutions of caffeine (10 mg/ml).

Drug release into an aqueous medium was followed spectrophotometrically using a temperature-controlled Caleva Dissolution Tester and a Cecil 9620 continuous flow UV-spectrophotometer. Results indicated the presence of low levels of drug, around 0.025 mg per stent. Release times were negligible, indicating a "burst effect of caffeine from the coating".

An additional experiment was conducted using caffeine in a higher concentration in the swelling solution, namely 10% w/w. No significant increase in loading levels or release half life.

Caffeine as a small (molecular weight 194 D) relatively hydrophilic (soluble at 1 g in 46 ml water at room temperature) releases at least 80% of its loading in the first 60 seconds. Such drugs are believed to be unsuitable for loading into zwitterionic polymers, for this reason.

EXAMPLE 3

Crosslinkable quater polymers were made from 2-methacryloyloxyethyl-2'-trimethylammoniumethyl phosphate inner salt, dodecylmethacrylate, 3-hydroxypropyl methacrylate and 3-(trimethoxysilyl)propyl methacrylate 27:55:15:3 (molar ratios), produced according to example 1-005 of WO-A-98/30615. Further polymers were formed as follows:

HEMA-PC:2-hydroxyethyl methacrylate:methyl methacrylate:methylene bis acrylamide (MBA) 12.5:67.22:20:0.28.

HEMA-PC:LM (lauryl methacrylate):methylene bis acrylamide (MBA) 1:2 or 1:1 HEMA-PC:LM with varying amounts of MBA ranging between 0.28 and 5.0 mole %.

HEMA-PC:LM:3-chloro-2-hydroxypropyl methacrylate (20:75:5).

The polymers including MBA were polymerised in situ to form crosslinked membranes. The polymers with crosslinkable groups (trimethoxysilylpropyl or 3-chloro-2-hydroxypropyl) were coated to form a membrane and subsequently crosslinked.

The crosslinked polymers were used to form "infinite slabs" type membranes, to simulate the coating on a stent.

In a first series of experiments, the HEMA-PC:HEMA:MMA:MBA copolymer was swollen in aqueous solutions of caffeine, dicloxacillin, vitamin B12, rhodamine and dipyridamole in water at room temperature over night.

The loaded levels were established to be the following:

TABLE 1

| Drug | Loading (mg/g polymer) |
|---|---|
| Caffeine | 80 |
| Vitamin B12 | 40 |
| Dicloxacillin | 32 |
| Rhodamine | 85 |
| Dipyridamole | 32 |

The profile of fractional release against square root of time for release into water (using the same equipment as example 2) are set out in FIG. 1. These profiles show that there is a fickian relationship between the fractional release and square root of time for the drugs. Caffeine, however, is released in an initial burst, with substantially total release after about an hour. The more hydrophobic drugs are released more slowly.

EXAMPLE 4

Effective Polymer Composition on Release of Dicloxacillin

The membrane formed based on a 1:4 copolymer of HEMA-PC and dodecylmethacrylate (LM) with 2 mole % of reactive monomer which is 3-chloro-2-hydroxypropyl methacrylate, was compared to the polymer crosslinked by diethylenically unsaturated monomer MBA used in example 3 above, to compare release rates to dicloxacillin, a medium molecular weight model drug. The release rates are shown in FIG. 2 which shows fractional release against square root of time.

The results show that, for the polymer having hydrophobic groups, the half life is much higher, even where the swelling figures and loadings were comparable.

EXAMPLE 5

Experiments on Release from Different Thickness Membranes of Caffeine

The membrane used in these experiments was that used in example 3 above, based on 0.28 mole % MBA. The membrane thicknesses tested were 0.57 and 0.87 mm. The membranes were swollen in an aqueous solution of caffeine. The release profiles are shown in FIG. 3.

EXAMPLE 6

Varying Cross-Linker Level

Polymers based on HEMA-PC:LM 1:2 with varying degrees of MBA crosslinker were tested to determine the effect of crosslinker on release of vitamin B12. The polymers were also tested for their water content when swollen to equilibrium in water at 37° C. The loading levels of vitamin B12 are recorded in table 2 below.

Also recorded in table 2 are similar results for MBA crosslinked copolymers based upon 1:1 copolymers of HEMA-PC and LM.

TABLE 2

| HEMA-PC:LM | Crosslinker (mole %) | Water Content (%) (37° C.) | Vitamin B12 Load (mg/g polymer) |
|---|---|---|---|
| 1:2 | 0.28 | 56 | 11.73 |
|  | 0.5 | 54 | 10.68 |
|  | 1 | 52 | 11.4 |
|  | 2 | 43 | 4.66 |
|  | 5 | 35 | 1.96 |
|  | 10 | 30 | 0 |
| 1:1 | 0.28 | 70 | 26.13 |
|  | 0.5 | 66 | 19.83 |
|  | 1 | 59 | 11.89 |
|  | 2 | 55 | 8.44 |
|  | 5 | 47 | 4.94 |

Figure 4:
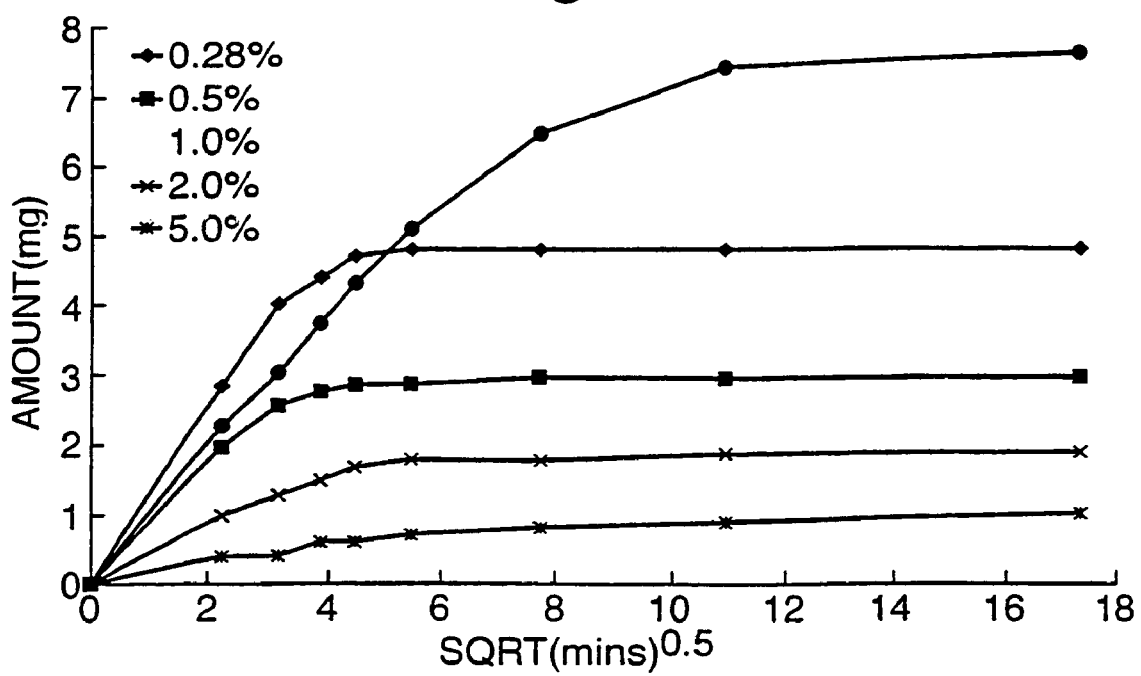
FIG. 4 represents Amount versus SQRT for Example 6.

The release profile for the 1:1 copolymer series are shown in FIG. 4.

EXAMPLE 7

The quater polymer synthesised as described above is formed into a membrane incured and loaded with caffeine and dipyridamole each from aqueous and 1:1 ethanol:water solutions, respectively. The release profiles are shown in accompanying FIG. 5.

Figure 5:
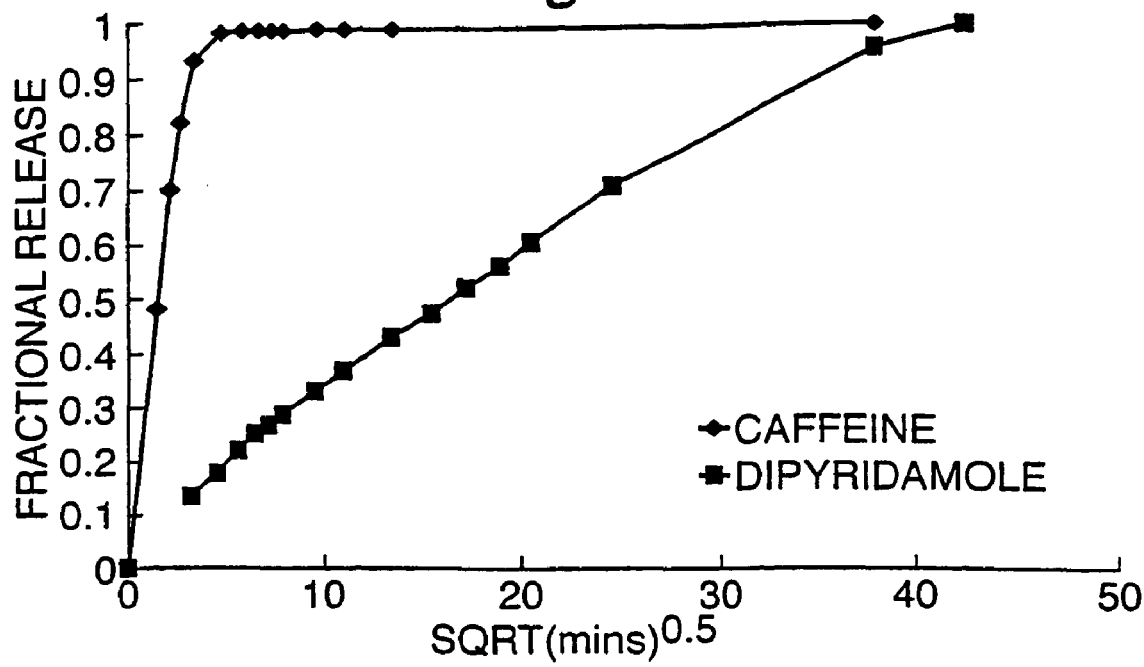
FIG. 5 represents Fractional Release versus SQRT for Example 7.

The half lives may be calculated from FIG. 5 which shows that the half life for caffeine release is 3 minutes while that for dipyridimole if 5 hours. The water content of the membrane when fully swollen in water at 37° C. is 56%. The total loading rates for the two model drugs are 28 mg/g polymer for caffeine and 18 mg/g polymer for dipyridimole.

EXAMPLE 8

HEMA-PC:LM 1:2 copolymer prepared as described in example 1, the HEMA-PC:LM:hydroxypropyl methacrylate:trimethoxysilylpropyl methacrylate quater polymer produced as in example 3 and an adaptation of the latter polymer but at mole ratios 27:27:35:12 were used to coat stents. The stents were biodiv Ysio stents and were coated using a dip coating rig which dips the stent and removes it from the coating solution at a rate of 5 mm/second and, after each dip step, dries the stent by sucking air through the lumen for about 1 minute. Multiple coatings were formed using different concentration polymer solutions as shown in the following table. The sucking of air through the central lumen results in lower coating thicknesses on the inside of the stent as shown by table 3. The coating solutions were, in each case, in ethanol. After coating the stents were dried at 70° C. for 16 hours during which time crosslinking takes place and subsequently sterilised by gamma radiation.

TABLE 3

| Stent Coating | Steps/concentration | Coating Thickness Process(approx.) | |
|---|---|---|---|
|  |  | Outside | Inside |
| —.2 | 8 × 25 mg/ml | 600 | 50 |
| —.2 | 4 × 50 mg/ml | 1100 | 600 |
| —.2 | 2 × 50 mg/ml | 800 | 300 |
| —.3 | 8 × 25 mg/ml | 700 | 50 |

Radio-labelled angiopeptin was custom prepared at Amersham International and supplied in an isotonic 0.05 M acetic acid solution at a concentration of 1 mg/ml. The solution was diluted to 500 μg/ml using isotonic 0.05 M acetic acid. The coated stents were placed in the solution and left at 37° C. for 30 minutes. The stents were then removed and allowed to dry at 40° C. for 30 minutes, before gamma counting to obtain total loading.

Water uptake was judged to be over 50% of the total water uptake at equilibrium.

Our results showed that increasing the period over which crosslinking takes place, the rate of swelling is reduced.

Figure 6:
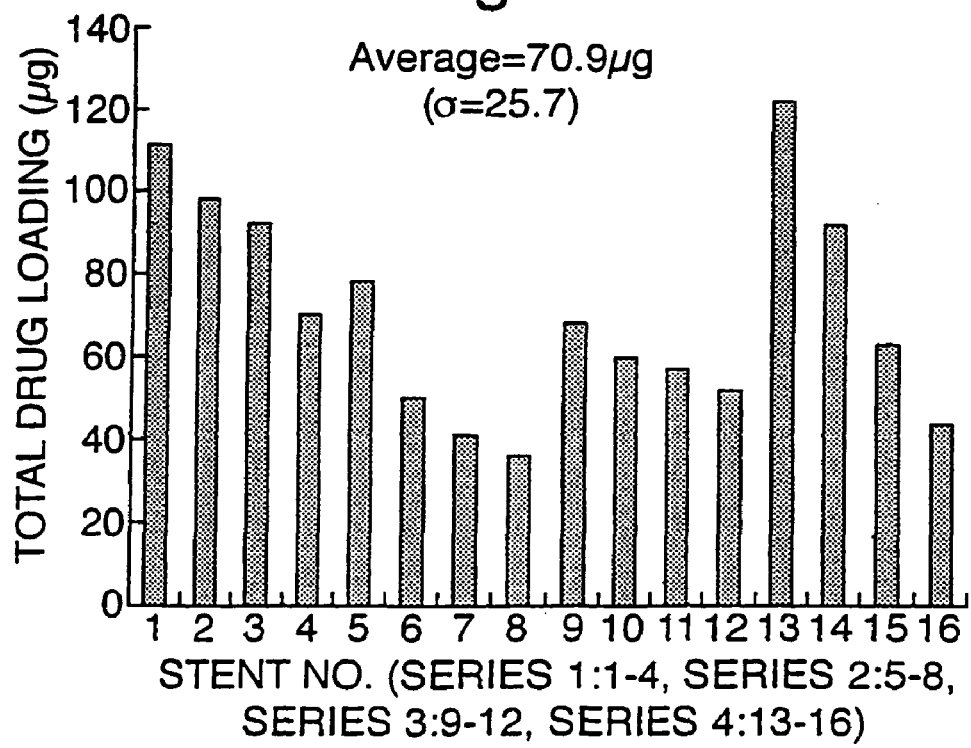
FIG. 6 represents a bar graph illustrating Total Drug Loading versus Stent No. (Series 1:1-4, Series 2:5-8, Series 3:9-12, Series 4:13-16) for Example 8.

The quater polymers used in the angiopeptin loading series were set out in table 4 below. The angiopeptin loadings are shown in FIG. 6.

TABLE 4

| Series | HEMA-PC | LM | Hpm | TMSPM |
|---|---|---|---|---|
| 1 | 13 | 39 | 15 | 5 |
|  | 53 | 39 | 15 | 5 |
|  | 13 | 55 | 15 | 5 |
|  | 33 | 55 | 15 | 5 |
| 2 | 13 | 39 | 15 | 9 |
|  | 33 | 39 | 15 | 9 |
|  | 13 | 55 | 15 | 9 |
|  | 33 | 55 | 15 | 9 |
| 3 | 13 | 39 | 35 | 5 |
|  | 33 | 39 | 35 | 5 |
|  | 13 | 55 | 35 | 5 |
|  | 33 | 55 | 35 | 5 |
| 4 | 13 | 39 | 35 | 9 |
|  | 33 | 39 | 35 | 9 |
|  | 13 | 55 | 35 | 9 |
|  | 33 | 55 | 35 | 9 |

EXAMPLE 9

Loading Cross-Linked Polymers with Taxol

Polymers of the same compositions as used in example 8 are tested for taxol (paclitaxel) loading. Twenty discs were cut out of each membrane of polymer, placed on pieces of PTFE in petri dishes and dried in an oven at 60° C. for an hour. When cool the discs were placed into a solution of taxol and allowed to swell in a water bath at 37° C. for half an hour. The taxol solution was decanted off, the discs labelled and placed on the PTFE and allowed to air dry. The discs were then tested for determining total loadings. The results are shown in table 5 below.

TABLE 5

| Series: Ex | Total Loading (µg per disc) | Standard Deviation |
|---|---|---|
| 1 | 35.2 | 3 |
|   | 80 | 8.2 |
|   | 15 | 2.4 |
|   | 18.1 | 3 |
| 2 | 51.7 | 2.4 |
|   | 57 | 9.8 |
|   | 18.6 | 2.8 |
|   | 10 | 14.7 |
| 3 | 55.2 | 20.2 |
|   | 11.2 | 10.6 |
|   | 5.4 | 3 |
|   | 25.3 | 5.4 |
| 4 | 23.8 | 6.8 |
|   | 60.5 | 2.6 |
|   | 24.3 | 1.8 |
|   | 64 | 3.9 |

EXAMPLE 10

Loading Stents Pre-Coated with Cross-Linked Polymer with Rapamycin

Rapamycin is a microlide having immunosuppresive properties. For instance it has been shown to have immunosuppresaent activity in an animal model of allograft rejection, by inhibiting T-cell activation. It has also been shown to block CD28-dependent stimulation. It has also been shown to apoptosis of cells by binding to intracellular SK506-binding protein. It has a molecular weight of 913, an a low solubility in water (5 mg/l), requiring ethanol in the swelling solution to assist solubilisation.

In the loading experiments, rapamycin was dissolved in 100% ethanol, at concentrations of 20, 50 and 55 g/l. Stents provided with the coatings as described in Reference Example 1 were loaded with rapamycin by being immersed in the respective solutions for periods of either 5 minutes or 30 minutes. The stents were subsequently removed from the rapamycin and wick dried on an absorbent tissue. The stents were subsequently allowed to dry for 30 minutes or more at room temperature. In addition, separately the stent, preloaded on a balloon catheter, was dipped for 5 minutes in the 55 g/l solution, and allowed to dry for 30 minutes at room temperature.

The loaded stents were subjected to elution studies at 25° C. and 37° C. The tests carried out at 25° C. involved individually placing the stents in vials containing 5 ml PBS and gently agitating the vials for a period of up to 2 hours. At time intervals samples of the buffer were tested for their rapamycin content, using HPLC.

The tests at 37° C. involved a flow system, with a flow of phosphate buffered saline being passed through channels, each containing one stent, the system being maintained at 37° C. In each channel, 2 stents were placed and 500 ml PBS were recirculated through the channel at a rate of 100 ml/min to minimise the circulation. The level of concentration of rapamycin in the solution, and remaining on the stent was determined.

For the premounted stent, elution studies, were not conducted, but the stent was expanded on the balloon, removed from the catheter and subjected to a test to determine the level of uptake of rapamycin.

The effects of drug loading time and concentration are shown in the following table 6:

TABLE 6

| | Unmounted stents | | |
|---|---|---|---|
| Rapamycin concentration in ethanol (100%) | Drug loading time/minutes | Stent size/mm | Total loading ISD/ µg per stent (no. Stents measured) |
| 20 | 30 | 18 | 47 ± 13 (4) |
| 50 | 5 | 15 | 172 ± 5 (2) |
| 55 | 5 | 15 | 142 ± 1 (3) |
| 55 | 30 | 15 | 104 ± 20 (3) |

The figures indicate that stents loaded from higher drug concentration solutions become loaded with higher levels of drugs. They also indicate that long loading times are not required and that 5 minutes is adequate.

The results of the elution tests using agitated PBS at 20° C. are shown in table 7 below

TABLE 7

| | | Unmounted stents | | |
|---|---|---|---|---|
| Test | | Elution Time/min | Rapamycin on stent/µg | Cumulative rapamycin eluted per stent/µg |
| 9.1 | Pre-elution | 0 | 47 ± 3 | 0 |
|   |   | 5 | — | 1.6 ± 0.5 |
|   |   | 15 | — | 7.4 ± 1.9 |
|   |   | 30 | — | 15.9 ± 3.1 |
|   | Post-elution | 60 | 37 ± 13 | 26.2 ± 3.3 |
| 9.2 | Pre-elution | 0 | 104 ± 20 | 0 |
|   |   | 5 | — | 1.0 ± 0.1 |
|   |   | 15 | — | 4.8 ± 0.2 |
|   |   | 30 | — | 10.2 ± 0.5 |
|   |   | 60 | — | 18.5 ± 1.2 |
|   | Post-elution | 120 | 84 ± 21 | 29.2 ± 1.7 |

The results indicate that there is a slow release of rapamycin over a period of 1 to 2 hours. For the stents having the higher initial loading (produced by loading for 30 minutes in a 55 g/l solution), there is still a high proportion of rapamycin remaining on the stent even after two hours. Both sets of results show that rapamycin elutes at a linear rate over the initial 2 hour period.

The flow elution tests indicate there is a steady release of rapamycin over 7 hours at 37° C. After 24 hours, more than 99% of total drug had eluted from the stent.

The tests carried out to determine the loading of pre-mounted stents indicated that on expansion of the stent, drug appeared to flake off the stent surface. Despite this, the loading levels achieved are substantially the same as the levels achieved by loading un-mounted stents of the same type.

EXAMPLE 11

Loading Stents Pre-Coated with Cross-Linked Polymer with Etoposide

The stents produced according to Reference Example 1 were loaded with etoposide, an anti-proliferative and anti-neoplastic agent, having a molecular weight of 589 D. It is only slightly soluble in water, though is soluble at sufficient levels for stent loading in a 50:50 (volume) mixture or ethanol and water. In this example it is dissolved in such a mixed solvent system at a concentration of 15 or 5 g/l and loaded onto the stent produced in Reference Example 1. For a biodiv Ysio 18 mm length stent (otherwise coated as described in Reference Example 1, the 15 g/l solution produced around 40 mg per stent (loaded from a 2 ml solution). Full loading appeared to be achieved after 15 minutes, and it proved unnecessary to raise the temperature. Drug elution tests indicate that a very high proportion of the etoposide is eluted into PBS after 15 minutes.

EXAMPLE 12

Loading Stents Precoated with Cross-Linked Polymer with Dexamethasone and Dexamethasone Phosphate Dexamethasone is a corticosteroid, a class of compounds known to be potent modulators of a range of cellular activities which may have activity of inhibiting restenosis. Thus dexamethasone has been shown to reduce reactive intimal hyperplasia in animal models of arterial injury. Systemic delivery of cortico steroids has failed to show a reduction in restinosis in humans and cortico steroids, administered systemically over extended periods of time may have potential adverse side affects. Delivery of dexamethasone from a stent directly to a vessel wall is believed to have potential benefit for efficacious performance. Dexamethasone phosphate has a molecular weight of 515.

BiodivYsio stents coated using the technique described in Reference Example 1, to provide a coating on the interior wall of around 350 nm thickness and on the exterior wall of around 1400 nm thickness, were loaded with dexamethasone phosphate from solutions in water of 1.0 g/l, 2.0 g/l and 5.0 g/l, leading to loadings of, respectively, 9 µg of dexamethasone phosphate per stent, 14 µg and 20 µg, the loading being conducted at 20 C. for 30 minutes. Elution tests carried out indicate that the rate of release of the drug is high, effectively all the drug being released within 1 hour, and the half life of the drug release being around 5 minutes.

Similar tests carried out on dexamethasone itself, which has a molecular weight of 390 D and is less water soluble than dexamethasone phosphate, indicates approximately the same level of loading under similar conditions, with a slower rate of release into aqueous medium. Thus the half life is around 10 minutes. Around 90% of dexamethasone has been released by around 3 hours.

EXAMPLE 13

Loading Stents Pre-Coated with Cross-Linked Polymer with Roxithromycin

Roxithromycin is a macrolide antibiotic having a molecular weight 840 D. It is prescribed for treatment of a variety of microbial infections in humans, including chlamydia. Recent research has shown a possible link between chlamydia infections and coronary artery disease in humans. Roxithromycin is substantially insoluble in water, though wholly soluble in ethanol. In ethanol/water mixtures, for instance 50:50 mixtures, a hazy solution is formed which is, however, suitable for loading stents.

Stents coated with polymer according to Reference Example 1 (15 mm) were loaded with roxithromycin from 5 g/l and 10 g/l solutions in ethanol or in ethanol:water 50:50 mixture. The level of loading of drug onto the stent was determined by elution from the stent into ethanol. It was found that the higher concentration solutions resulted in higher loadings of roxithromycin, whilst the selection of ethanol or ethanol:water made little difference to the loading level. The average loading for the 5 g/l solution was 58 µg per stent, whilst the 10 g/l solutions lead to loadings of around 70 µg for both solvent systems.

Stents loaded from the 10 g/l ethanolic solutions were subsequently contacted with phosphate buffered saline under gentle agitation and the release rate determined. The release profile showed that the compound released very slowly, around half the compound having been released after 24 hours. The test was continued up to 48 hours, after which time 5 to 10% of roxithromycin remains in the coating.

EXAMPLE 14

Loading Stents Pre-Coated with Cross-Linked Polymer with Aspirin

Aspirin has anti platelet activity, which may be useful delivered locally from a stent. Aspirin has a molecular weight of 180 D. Aspirin was dissolved at 10 gm/l or 40 gm/l in ethanol (being only partially soluble in water). The solutions were used to load 15 mm stents having coatings produced according to Reference Example 1 (interior wall coating thickness around 350 nanometers, exterior wall coating thickness around 1400 nanometers). The stents were immersed in the aspirin solutions at room temperature for a period of one hour. The stent was removed from the solution, excess solution removed by gentle dabbing with absorbent tissue. Aspirin loading levels were determined by extracting the aspirin into 3 ml ethanol. The results indicated that around 10 µg aspirin is loaded for the 10 g/l concentration whilst around 40 µg aspirin is loaded for the 40 g/l solution.

Release of aspirin from the stent into phosphate buffered saline indicated that around 90% of the drug had eluted after about 1 hour.

EXAMPLE 15

Loading Stents Pre-Coated with Cross-Linked Polymer with Tetradecylthioacetic Acid Tetradecylthioacetic acid (TTA) is a compound having a molecular weight of 288 D. It has been identified to have anti-inflammatory properties. It is substantially insoluble in the water. TTA was dissolved in ethanol at concentrations of 10, 25 and 50 g/l and the solutions were conducted with biodivYsio stents (18 mm) coated according to the technique in Reference Example 1 below, to have a coating thickness on the interior wall of around 350 nm and a thickness 1400 nm on the exterior wall. The stents were immersed in the alcoholic TTA solutions for 30 minutes, removed and allowed to dry in air at ambient temperature for 5 minutes. The loading levels were determined and found to be around 90 µg per stent for the 50 g/l concentration, 30 µg per stent for 25 g/l and 20 µg per stent for the 10 g/l solutions, respectively.

Several stents loaded from the 50 gm/l solution were tested for their rate of elution into phosphate buffered saline, at 37° C., in a flow system as described above in Example 10. The extent of release was determined in the elution tests after periods in the range 1 to 48 hours, by extracting residual TTA from the stent into chloroform. The results of the elution test are shown in Table 8 below.

TABLE 8

| Time point (hours) | TTA content per stent (µg/stent) |
|---|---|
| 0 | 100 |
| 1 | 40 |
| 4 | 35 |
| 8 | 6 |

TABLE 8-continued

| Time point (hours) | TTA content per stent (µg/stent) |
|---|---|
| 24 | 2 |
| 48 | 0.2 |

The loading levels at different concentrations was carried out on 15 mm stents, whilst the elution rates are done 18 mm stents.

Figure 7:
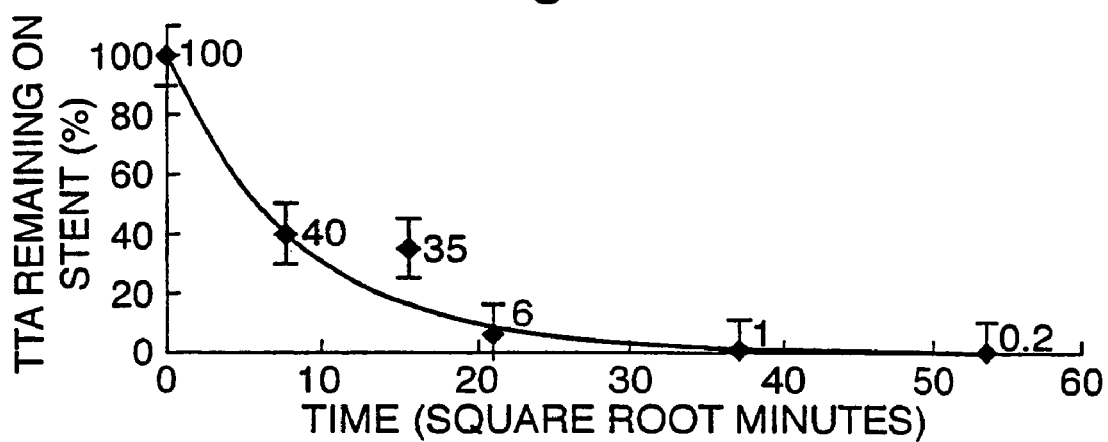
FIG. 7 represents percentage TTA remaining on Stent versus Time for Example 15.

The results of the elution tests, shown in FIG. 7, show that initial release of TTA is rapid, with release continuing over the period up to 48 hours. More than 90% of the drug appears to have been released at 8 hours.

EXAMPLE 16

Ex Vivo and In Vivo Tests on Angiopeptin a) Ex Vivo Tests

More extensive work was conducted on angiopeptin loaded stents, to mimic the in vivo environment. The further examples use an ex vivo human saphenous vein model (as described by Armstrong, J. et al 1998. A purfused organ culture model to investigate drug release from coronary stents, Northern General Hospital, Sheffield (in press). The stents (produced as in Reference Example 1 below) were loaded using aqueous solutions of angiopeptin labeled with $^{125}$I by the chloramine T method, into which the stent was dipped for half an hour at 37 C. The loaded stents were then allowed to air dry for one hour. Stents were in inserted into the vein, expanded by balloon catheter, washed in 10 ml culture medium for 10 s then placed in the purpose-built organ culture chamber bathed in 30 ml culture medium. The chamber was then connected to a circuit and 100 ml culture medium (HEPES-buffered RPMI 1640 culture medium (LIFE) supplemented with penicillin (100 µl/ml) streptomycin (100 units/ml) and glutamine (2 mM)) at 70 ml/min, then removed after 1 hour or 24 hours. The stent was subsequently examined to determine the proportion of angiopeptin which has eluted, whilst the vessel immediately surrounding the stent was investigated to determine the proportion of eluted drug found in the vessel. The culture medium was also analysed as was the explanted stent for radio activity.

After 1 hour, 93% of angiopeptin had eluted, of which 13.9% was in the surrounding vessel concentrated at the stented region. After 24 hours, 97% of drug has eluted, of which 7.4% remained in the vessel concentrated around the stented region. At both times the angiopeptin level in the downstream portion of vessel was higher than in the upstream portion. The results indicate that the angiopeptin can be delivered into human vascular tissue. The released angiopeptin efficiently enters the vessel surrounding the stent. Euluted angiopeptin is found in the culture medium but some may adsorb onto the apparatus.

b) In Vivo Tests

Further work was conducted to investigate the ability of the angiopeptin loaded stents to deliver angiopeptin tissue in an in vivo, in a porcine coronary artery model. Stents produced as described in Reference Example 1 were dipped into aqueous solution of $^{125}$I-angiopeptin as in stents were deployed in the coronary artery and then removed after 1 hour, 24 hours, 7 days or 28 days. The levels of angiopeptin remaining in the arterial wall immediately surrounding the stent was determined as well as the level recovered in blood and urine.

After 1 hour, the level of angiopeptin in tissue was around pg/ml tissue. After 24 hours, the level of angiopeptin was around 400 pg/ml, whilst at 7 days the level had reduced to around 360 pg/ml. At 28 days the level was around 200 pg/ml. After 5 min angiopeptin could be identified in blood (at 0.08 µg/ml), the level being about the same after one hour and reduced to around 0.01 µg/ml after 24 hours. No angiopeptin could be found in blood at 7 to 28 days. Angiopeptin appeared at 0.29 µg/ml in urine after 1 hour, low levels (0.01 µg/ml) still being detectable in urine after 28 days.

Tissue distribution investigations indicate that at 1 hour, 84% of released angiopeptin is localised in the left anterior descending coronary artery. At the longer time points, 1 to 28 days, the angiopeptin is localised to a greater extent in the central section of LAD surround the stent. At these time points, less than 1% of the detected angiopeptin is located in tissue other than the heart. After 1 hour, 9% of the angiopeptin remained on the stent, after 24 hours 4% of the angiopeptin remained and after 7 days, 1.5% of the angiopeptin remained on the stent.

Conclusion

Extrapolation of these results for angiopeptin to other drugs, comparing in vitro elution rates ex vivo and in vivo, allow a prediction that the release of drug will be extremely localised to surrounding tissue, rather than to the circulation. Furthermore the drug will be retained at the delivery site over extended periods of time. It appears that angiopeptin is eluted very quickly into the system initially, presumably by elution from the lumenal (interior wall) surface of the stent.

EXAMPLE 17

Coating Stents with Etoposide/Polymer Premixes

In this example, rather than precoating the polymer according to reference Example 1, followed by loading of drug, a premix of drug and crosslinkable polymer is formed and coated onto a stent. The crosslinkable polymer is identical to that used in Reference Example 1, 0.932 g polymer being dissolved into a 1:1 ethanol:water (by volume) mixture (50 ml). 0.06 g etoposide was dissolved into the solution and the mixed coating solution coated onto a stent using the same technique as in Reference Example 1, to produce a thicker coating on the outside as compared to the inside. The coated stents were cured overnight at a temperature in the range 50 to 70 C.

The amount of drug loaded into the stents was determined by elution into an ethanol:water 50:50 (volume) mixture. The results indicated an average etoposide loading of around 12 µg per stent. If it is assumed that the weight of mixed coating is the same as the weight achieved by the technique of reference Example 1 would lead to a prediction that around 9 to 13 µg per stent of etoposide would be expected to be deposited. The amount of etoposide eluted into ethanol:water is in this range. This is believed to indicate that crosslinking of the polymer in the presence of drug does not change the drug chemically, nor inhibit full elution.

Stents produced by the above technique were also tested to determine the rate of release of etoposide into 5 ml phosphate buffered saline, indicated that the initial rate of release was fast and plateaued at around 5 minutes, this being presumed to represent substantially full release. The release rate, from the results, for the stent coated with a polymer crosslinked in the presence of drug indicate that the release of drug may not be slowed down as compared to the alternative system, where precoated stents are contacted with a solution of drug.

EXAMPLE 18

Ex Vivo Tests on Polymer/Dipyridamole Coated Stents

Palmaz-Schatz Stents (trade mark) were coated with a solution of the same polymer as used in Reference Example 1, dissolved in ethanol at 50 g/l concentration, also containing dipyridamole at 30 g/l concentration. Stents were dipped into the solution by hand, using several coating steps. The stents were then cured overnight at 70 C. in moist air.

The coated stents were tested in an ex vivo model using fresh human saphenous vein, previously washed in the same culture medium as is used in Example 16 above, in the ex vivo tests. The stents were delivered into veins, which were subsequently deposited into apparatus used in Example 16. The circulating liquid, and the vessel wall were analysed at 1, 6 or 24 hours to determine localisation of dipyridamole. Dipyridamole can be detected in the circulating medium after one hour, the level increasing over the twenty four hour test period. Similarly, the level of dipyridamole remaining on the stent decreases from 1 hour to 24 hours. Using the detection techniques, no dipyridamole could be seen within the vessel wall until twenty four hours after stent deployment. At this time, dipyridamole is concentrated in the section of the vein immediately surrounding the stent with lower levels in the vessel immediately adjacent those sections.

These results indicate that drug is released from a coating which has been crosslinked in the presence of the drug.

REFERENCE EXAMPLE 1

Asymmetric Coating of Stents with Cross-Linkable Zwitterionic Polymer

In this example, the production of polymer coated stents having a thicker coating on the outer surface, is described. 15 mm (length) biodivYsio stents, formed of 316L stainless steel are coated with solutions of a crosslinkable polymer formed from 2-methacryloxy-2'-trimethylamoniumethylphosphate inner salt (23 parts by mole), dodecylmethacrylate (47 parts by mole), 3-hydroxypropylmthacrylate (25 parts by mole) and 3-trimethoxysilylpropylmethacrylate (5 parts by mole) in ethanol. The quater polymer was synthesised as described in WO-A-9830615. The stents were coated using the apparatus described in WO-A-0004999, followed by curing overnight by maintaining the stents at a temperature of in the range 50-70° C. The thickness of the coating on the struts on the interior and exterior surfaces was determined using an atomic force microscope. The conditions were varied, by changing one or more of the following features: polymer concentration (between 10 and 50 g/l), the speed at which the stent is dipped into and removed from the coating solution, the pressure difference between the perforated needle positioned in the lumen of the stent and the space outside the stent wall, the number of coating steps and the period for which each coating is allowed to dry between coating steps. The effect of the changes on the thickness of the coating on the interior and exterior surfaces of the struts, as well as the avoidance of bridging or webbing between the struts was optimised. The conditions were selected so as to achieve an average coating thickness on the internal wall of around 350 nm, and an average thickness on the external wall of around 1400 nm.

In the optimisation tests, the conditions tested allowed the ratio of the thickness of the interior and exterior walls to be varied in the range 1:(1.5 to 10). The coating on the interior wall was varied between about 40 and about 900 nm. The thickness on the exterior wall was varied between about 400 and about 1500 nm.

These stents were used in drug delivery tests of the above Examples.

REFERENCE EXAMPLE 2

Asymmetric Coating of Stents with Other Polymers

Using the same general coating technique as described for Reference Example 1, biodivysio stents were coated using solutions of different polymers in appropriate solvent systems. In each case the polymer concentration was 2% weight/volume. The following polymer:solvent combinations were used:

polyethyleneglycol (10,000 D average molecular weight) in ethanol:water (1:1 volume)
poly(DL-lactide-co-glycolide) in chloroform
nylon 6/6 (poly(hexamethylene adipamide)) in trifluoroethanol
Tecoflex (trade mark) (polyurethane) in tetrahydrofuran
poly(3-hydroxybutyric acid-co-3-hydroxyvaleric acid) (5% PHV) in chloroform
poly(acrylic acid) in ethanol:water (1:0.06 volume).

The coated stents were dried in an appropriate manner. After coating the average thickness on the interior and exterior wall surfaces were determined using atomic force microscopy. The results indicated that, whilst the actual thicknesses differed between the various polymers, all formed asymmetric coating thickness, with thicker coatings on the exterior wall surface. The ratio of thickness between inside and outside was 1:(2 to 6). The polyethyleneglycol produced the lowest exterior wall thickness at 420 nm, whilst the polyacrylic acid formed the thickest exterior surface at 2.3 µm.

The asymmetric coated stents could be used in the novel process in which the coating is swollen by contact with a drug-containing solution in a suitable solvent, or by coating the stent with a mixed solution of polymer and drug.

The invention claimed is:

1. A process for producing an implant, for immediate implant into a patient, that is loaded with a pharmaceutically active agent comprising the steps:
   a) providing a sterile coated implant comprising a biostable implant and a coating comprising a polymer matrix which has pendant zwitterionic groups;
   b) providing a pharmaceutical solution comprising a pharmaceutically active agent in solution in a solvent which is capable of swelling the coating;
   c) contacting the coated implant with the pharmaceutical solution at a temperature and for a time to allow swelling of the coating to an extent in the range 25 to 95% of the equilibrium swelling at 37° C. in the pharmaceutical solution; and
   d) drying the treated implant by solvent evaporation to remove 10 to 100% of total solvent, to produce a pharmaceutically active loaded implant,
   wherein providing the sterile coated implant comprises:
   a1) coating a biostable implant with a coating composition containing the polymer of the matrix, or a precursor thereof,
   a2) curing the polymer to form the said polymer matrix; and
   a3) sterilising the implant coated with the polymer matrix.

2. A process according to claim 1 in which the polymer matrix is substantially non-biodegradable.

3. A process according to claim 2 in which the polymer matrix is covalently crosslinked and/or bound to the implant surface.

4. A process according to claim 2 in which the coating composition contains a cross-linkable polymer and in which curing involves cross-linking the polymer.

5. A process according to claim 2 in which the polymer in the coating composition is formed from ethylenically unsaturated monomers including a zwitterionic monomer.

6. A process according to claim 5 in which the ethylenically unsaturated monomers include a surface binding monomer, selected from a hydrophobic comonomer, a reactive monomer having one or more pendant reactive groups capable of forming intermolecular cross-links, and mixtures thereof.

7. A process according to claim 5 in which the zwitterionic monomer has the general formula I:

$$YBX \quad\quad I$$

wherein
   B is selected from the group consisting of straight and branched alkylene, alkylene-oxaalkylene and alkylene oligo-oxaalkylene chains optionally containing one or more fluorine atoms up to and including perfluorinated chains and, if X or Y contains a terminal carbon atom bonded to B, a valence bond;
   X is a zwitterionic group; and
   Y is an ethylenically unsaturated polymerisable group selected from the group consisting of

[structures: $H_2C=C(R)-C(O)-A-$ and para-substituted styrene with K substituent]

$CH_2$=C(R)$CH_2$O—, $CH_2$=C(R)$CH_2$OC(O)—, $CH_2$=C(R)OC(O)—, $CH_2$=C(R)O—, $CH_2$=C(R)$CH_2$OC(O)N(R$^1$)—, R$^2$OOCCR=CRC(O)O—, RCH=CHC(O)O—, RCH=C(COOR$^2$)$CH_2$C(O)O—,

[two cyclic structures: RHC=C-C(O)-N—CH$_2$-C(O) ring, and RC=C-C(O)-N—RC=C-C(O) ring] and wherein:
   R is hydrogen or a $C_1$-$C_4$ alkyl group;
   R$^1$ is hydrogen or a $C_1$-$C_4$ alkyl group or R$^1$ is —B—X where B and X are as defined above; and
   R$^2$ is hydrogen or a $C_{1-4}$ alkyl group;
   A is —O— or —NR$^1$—;
   K is selected from the group consisting of —(CH$_2$)$_p$OC(O)—, —(CH$_2$)$_p$C(O)O—, —(CH$_2$)$_p$OC(O)O—, —(CH$_2$)$_p$NR$^3$—, —(CH$_2$)$_p$NR$^3$C(O)—, —(CH$_2$)$_p$C(O)NR$^3$—, —(CH$_2$)$_p$NR$^3$C(O)O—, —(CH$_2$)$_p$OC(O)NR$^3$—, —(CH$_2$)$_p$NR$^3$C(O)NR$^3$— (in which the groups R$^3$ are the same or different), —(CH$_2$)$_p$O—, —(CH$_2$)$_p$SO$_3$—, and, optionally in combination with B, a valence bond
   p is from 1 to 12; and
   R$^3$ is hydrogen or a $C_1$-$C_4$ alkyl group.

8. A process according to claim 7 in which X is a group of the general formula V

[structure showing phosphate group with X$^3$, X$^4$, W$^+$, O$^-$] V in which X$^3$ and X$^4$, which are the same or different, are selected from the group consisting of —O—, —S—, —NH— and a valence bond, and W$^+$ is selected from the group consisting of —W$^1$—N$^+$R$^{11}{}_3$, —W$^1$—P$^+$R$^{11}{}_3$, —W$^1$—S$^+$R$^{11}{}_2$ or —W$^1$-Het$^+$ in which:

W$^1$ is selected from the group consisting of alkanediyl of 1-6 carbon atoms optionally containing one or more ethylenically unsaturated double or triple bonds, disubstituted-aryl, alkylene aryl, aryl alkylene, alkylene aryl alkylene, disubstituted cycloalkyl, alkylene cycloalkyl, cycloalkyl alkylene and alkylene cycloalkyl alkylene, which group W$^1$ optionally contains one or more fluorine substituents and/or one or more functional groups; and either the groups R$^{10}$ are the same or different and each is selected from the group consisting of hydrogen, alkyl of 1 to 4 carbon atoms and aryl, or two of the groups R$^{10}$ together with the nitrogen atom to which they are attached form a heterocyclic ring containing from 5 to 7 atoms or the three groups R$^{10}$ together with the nitrogen atom to which they are attached form a fused ring structure containing from 5 to 7 atoms in each ring, and optionally one or more of the groups R$^{10}$ is substituted by a hydrophilic functional group, and the groups R$^{11}$ are the same or different and each is R$^{10}$ or a group OR$^{10}$, where R$^{10}$ is as defined above; and Het is selected from the group consisting of aromatic nitrogen-, phosphorus- and sulphur-containing rings.

9. A process according to claim 8 in which X is a group of formula VI:

[structure showing phosphate group with —O—, O$^-$, and —O—(CH$_2$)$_e$NR$^{12}{}_3{}^+$] VI where the groups R$^{12}$ are the same or different and each is hydrogen or $C_{1-4}$ alkyl, and e is from 1 to 4.

10. A process according to claim 9 in which each group R$^{12}$ is methyl, and in which e is 2 or 3.

11. A process according to claim 5 in which the surface binding monomer has the general formula VII $$Y^1R^{13} \quad\quad VII$$

wherein $Y^1$ is selected from the group consisting of

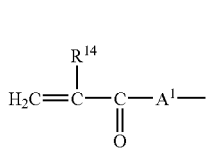 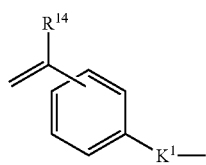

$CH_2=C(R^{14})CH_2O-$, $CH_2=C(R^{14})CH_2OC(O)-$, $CH_2=C(R^{14})OC(O)-$, $CH_2=C(R^{14})O-$, $CH_2=C(R^{14})CH_2OC(O)N(R^{15})-$, $R^{16}OOCCR^{14}=CR^{14}C(O)O-$, $R^{14}CH=CHC(O)O-$, $R^{14}CH=C(COOR^{16})CH_2C(O)O-$,

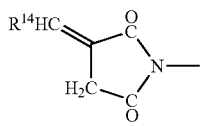 and 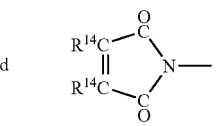

wherein:
$R^{14}$ is hydrogen or a $C_1$-$C_4$ alkyl group;
$R^{15}$ is hydrogen or a $C_1$-$C_4$ alkyl group or $R^{15}$ is $R^{13}$;
$R^{16}$ is hydrogen or a $C_{1-4}$ alkyl group;
$A^1$ is $-O-$ or $-NR^{15}-$; and
$K^1$ is selected from the group consisting of $-(CH_2)_qOC(O)-$, $-(CH_2)_qC(O)O-$, $-(CH_2)_qOC(O)O-$, $-(CH_2)_qNR^{17}-$, $-(CH_2)_qNR^{17}C(O)-$, $-(CH_2)_qC(O)NR^{17}-$, $-(CH_2)_qNR^{17}C(O)O-$, $-(CH^2)_qOC(O)NR^{17}-$, $-(CH_2)_qNR^{17}C(O)NR^{17}-$ (in which the groups $R^{17}$ are the same or different), $-(CH_2)_qO-$, $-(CH_2)_qSO_3-$, and a valence bond
q is from 1 to 12;
and $R^{17}$ is hydrogen or a $C_1$-$C_4$ alkyl group;
and $R^{13}$ is a surface binding group, selected from hydrophobic groups and ionic groups.

12. A process according to claim 11 in which $R^{13}$ is a straight chain alkyl having 8 to 18 carbon atoms.

13. A process according to claim 5 in which the reactive monomer has the general formula VIII $Y^2B^2R^{20}$      VIII wherein
$B^2$ is selected from the group consisting of straight or branched alkylene, oxaalkylene and oligo-oxaalkylene chain optionally containing one or more fluorine atoms up to and including perfluorinated chains, and a valence bond;
$Y^2$ is an ethylenically unsaturated polymerisable group selected from the group consisting of

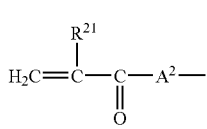 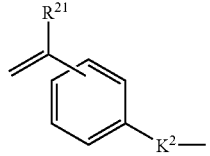

$CH_2=C(R^{21})CH_2-O-$, $CH_2=C(R^{21})CH_2OC(O)-$, $CH_2=C(R^{21})OC(O)-$, $CH_2=C(R^{21})O-$, $CH_2=C(R^{21})CH_2OC(O)N(R^{22})-$, $R^{23}OOCCR^{21}=CR^{21}C(O)O-$, $R^{21}H=CHC(O)O-$, $R^{21}H=C(COOR^{23})CH_2C(O)O-$

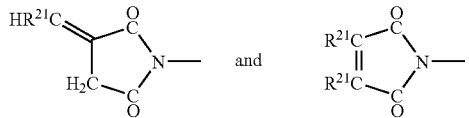

and where
$R^{21}$ is hydrogen or $C_1$-$C_4$ alkyl;
$R^{23}$ is hydrogen, or a $C_{1-4}$-alkyl group;
$A^2$ is $-O-$ or $-NR^{22}-$;
$R^{22}$ is hydrogen or a $C_1$-$C_4$ alkyl group or $R^{22}$ is a group $B^2R^{20}$;
$K^2$ is selected from the group consisting of $-(CH_2)_kOC(O)-$, $-(CH)_kC(O)O-$, $-(CH_2)_kOC(O)O-$, $-(CH_2)_kNR^{22}-$, $-(CH_2)_kNR^{22}C(O)-$, $-(CH_2)_kOC(O)O-$, $-(CH_2)_kNR^{22}-$, $-(CH_2)_kNR^{22}C(O)-$, $-(CH_2)_kC(O)NR^{22}-$, $-(CH_2)_kNR^{22}C(O)O-$, $-(CH_2)_kOC(O)NR^{22}-$, $-(CH_2)_kNR^{22}C(O)NR^{22}-$ (in which the groups $R^{22}$ are the same or different), $-(CH_2)_kO-$, $-(CH_2)_kSO_3-$, and a valence bond and k is from 1 to 12; and
$R^{20}$ is a cross-linkable group.

14. A process according to claim 13 in which $R^{20}$ is selected from the group consisting of ethylenically and acetylenically unsaturated groups containing radicals; aldehyde groups; silane and siloxane groups containing one or more substituents selected from halogen atoms and $C_{1-4}$ alkoxy groups; hydroxyl; amino; carboxyl; epoxy; $-CHOHCH_2Hal$ (in which Hal is selected from chlorine, bromine and iodine atoms); succinimido; tosylate; triflate; imidazole carbonyl amino; optionally substituted triazine groups, acetoxy; mesylate; carbonyl di(cyclo)alkyl carbodiimidoyl; isocyanate, acetoacetoxy; and oximino.

15. A process according to claim 14 in which $R^{20}$ comprises a silane group containing at least one substituent selected from halogen atoms and $C_{1-4}$-alkoxy groups.

16. A process according to claim 15 in which $R^{20}$ is a trimethoxysilyl group.

17. A process according to claim 1 in which the thickness of the coating of polymer matrix of the sterile coated implant is in the range 500 nm to 500 μm.

18. A process according to claim 1 in which step c) is conducted at about 37° C.

19. A process according to claim 1 in which step c) is conducted over a period in the range 1 min to 30 min.

20. A process according to claim 1 in which the implant is a stent, a stent-graft or a vascular graft.

21. A process according to claim 20 in which the implant is a vascular stent.

22. A process according to claim 21 in which both inner and outer surfaces of the stent are coated with polymer matrix and both polymer coated surfaces are contacted with pharmaceutical solution in step c).

23. A process according to claim 22 in which the ratio of thickness of polymer matrix on the outer to the inner surface is (at least 1.5):1.

24. A process according to claim 1 in which the pharmaceutically active agent is selected from the group consisting of dipyridamole, angiopeptin, taxol, roxithromycin, rapamycin, tetradecylthioacetic acid, aspirin, etoposide and dexamethasone.

25. A process for producing an implant loaded with a pharmaceutically active agent comprising the steps:
i) providing an implant selected from a graft, a stent and a stent-graft having a polymer matrix coating on its inner and outer surfaces, the said polymer of the matrix being a cross-linked polymer formed from ethylenically unsaturated monomer including a) a zwitterionic monomer of the general formula I $$YBX \qquad\qquad I$$

wherein
- B is selected from the group consisting of straight and branched alkylene, alkylene-oxaalkylene and alkylene oligo-oxaalkylene chain optionally containing one or more fluorine atoms up to and including perfluorinated chains and, if X or Y contains a terminal carbon atom bonded to B, a valence bond;
- X is a zwitterionic group; and
- Y is an ethylenically unsaturated polymerisable group selected from the group consisting of

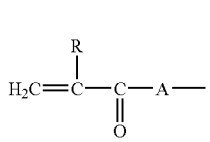 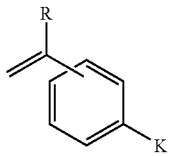

$CH_2=C(R)CH_2O—$, $CH_2=C(R)CH_2OC(O)—$, $CH_2=C(R)OC(O)—$, $CH_2=C(R)O—$, $CH_2=C(R)CH_2OC(O)N(R^1)—$, $R^2OOCCR=CRC(O)O—$, $RCH=CHC(O)O—$, $RCH=C(COOR^2)CH_2C(O)O—$,

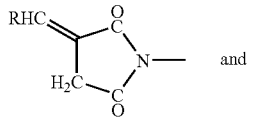 and 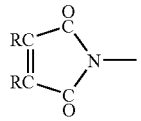

wherein:
- R is hydrogen or a $C_1$-$C_4$ alkyl group;
- $R^1$ is hydrogen or a $C_1$-$C_4$ alkyl group or $R^1$ is —B—X where B and X are as defined above; and
- $R^2$ is hydrogen or a $C_{1-4}$ alkyl group;
- A is —O— or —$NR^1$—;
- K is selected from the group consisting of —$(CH_2)_pOC(O)$—, —$(CH_2)_pC(O)O$—, —$(CH_2)_pOC(O)O$—, —$(CH_2)_pNR^3$—, —$(CH_2)_pNR^3C(O)$—, —$(CH_2)_pC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, and, optionally in combination with B, a valence bond
- p is from 1 to 12; and
- $R^3$ is hydrogen or a $C_1$-$C_4$ alkyl group;

b) a surface binding monomer of the general formula VII $$Y^1R^{13} \qquad\qquad VII$$

wherein $Y^1$ is selected from the group consisting of

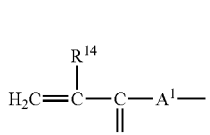 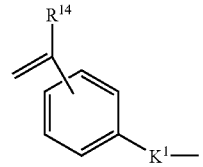

$CH_2=C(R^{14})CH_2O—$, $CH_2=C(R^{14})CH_2OC(O)—$, $CH_2=C(R^{14})OC(O)—$, $CH_2=C(R^{14})O—$, $CH_2=C(R^{14})CH_2OC(O)N(R^{15})—$, $R^{16}OOCCR^{14}=CR^{14}C(O)O—$, $R^{14}CH=CHC(O)O—$, $R^{14}CH=C(COOR^{16})CH_2C(O)—)—$,

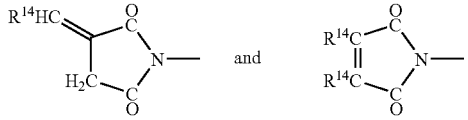

wherein:
- $R^{14}$ is hydrogen or a $C_1$-$C_4$ alkyl group;
- $R^{15}$ is hydrogen or a $C_1$-$C_4$ alkyl group or $R^{15}$ is $R^{13}$;
- $R^{16}$ is hydrogen or a $C_{1-4}$ alkyl group;
- $A^1$ is —O— or —$NR^{15}$—, and
- $K^1$ is selected from the group consisting of —$(CH_2)_qOC(O)$—, —$(CH_2)_qC(O)O$—, —$(CH_2)_qOC(O)O$—, —$(CH_2)_qNR^{17}$—, —$(CH_2)_qNR^{17}C(O)$—, —$(CH_2)_qC(O)NR^{17}$—, —$(CH_2)_qNR^{17}C(O)O$—, —$(CH_2)_qOC(O)NR^{17}$—, —$(CH_2)_qNR^{17}C(O)NR^{17}$— (in which the groups $R^{17}$ are the same or different), —$(CH_2)_qO$—, —$(CH_2)_qSO_3$—, and a valence bond
- q is from 1 to 12;
- and $R^{17}$ is hydrogen or a $C_1$-$C_4$ alkyl group;
- and $R^{13}$ is a surface binding group, selected from hydrophobic groups and ionic groups; and c) a reactive monomer of the general formula VIII $$Y^2B^2R^{20} \qquad\qquad VIII$$

wherein
- $B^2$ is selected from the group consisting of straight and branched alkylene, oxaalkylene and oligo-oxaalkylene chain optionally containing one or more fluorine atoms up to and including perfluorinated chains, and a valence bond;
- $Y^2$ is an ethylenically unsaturated polymerisable group selected from the group consisting of

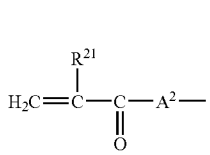 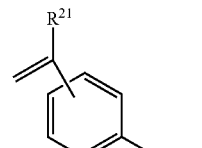

$CH_2=C(R^{21})CH_2—O—$, $CH_2=C(R^{21})CH_2OC(O)—$, $CH_2=C(R^{21})OC(O)—$, $CH_2=C(R^{21})O—$, $CH_2=C(R^{21})CH_2OC(O)N(R^{22})—$, $R^{23}OOCCR^{21}=CR^{21}C(O)O—$, $R^{21}H=CHC(O)O—$, $R^{21}H=C(COOR^{23})CH_2C(O)O—$

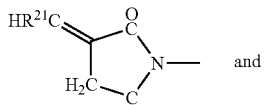

where
- $R^{21}$ is hydrogen or $C_1$-$C_4$ alkyl;
- $R^{23}$ is hydrogen, or a $C_{1-4}$-alkyl group;
- $A^2$ is —O— or —$NR^{22}$—;

$R^{22}$ is hydrogen or a $C_1$-$C_4$ alkyl group or $R^{22}$ is a group $B^2R^{20}$;

$K^2$ is selected from the group consisting of —$(CH_2)_kOC(O)$—, —$(CH)_kC(O)O$—, —$(CH_2)_kOC(O)O$—, —$(CH_2)_kNR^{22}$—, —$(CH_2)_kNR^{22}C(O)$—, —$(CH_2)_kOC(O)O$—, —$(CH_2)_kNR^{22}$—, —$(CH_2)_kNR^{22}C(O)$—, —$(CH_2)_kC(O)NR^{22}$—, —$(CH_2)_kNR^{22}C(O)O$—, —$(CH_2)_kOC(O)NR^{22}$—, —$(CH_2)_kNR^{22}C(O)NR^{22}$— (in which the groups $R^{22}$ are the same or different), —$(CH_2)_kO$—, —$(CH_2)_kSO_3$—, and a valence bond and k is from 1 to 12; and $R^{20}$ is a silyl group having three alkoxy substituents;

and the thickness of the coating being in the range of 500 nm to 500 μm, wherein the outer surface of the stent is provided with a thicker coating of cross-linkable polymer than the inner surface wherein the ratio of the thickness of the coating on the outer surface to the inner surface is in the range of (at least 1.5):1;

ii) providing a pharmaceutical solution comprising a pharmaceutically active agent having a molecular weight of up to 1200 D in solution in a solvent which is capable of swelling the coating;

iii) contacting the coated implant with the pharmaceutical solution; and iv) drying the treated implant by solvent evaporation to remove 10 to 100% of total solvent, to produce a pharmaceutically active loaded implant.

26. A process according to claim 25 in which X is a group of formula VI:

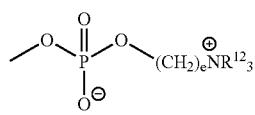

VI where the groups $R^{12}$ are the same or different and each is hydrogen or $C_{1-4}$ alkyl, and e is from 1 to 4.

27. A process according to claim 26 in which B is $C_{2-6}$ alkanediyl and Y is $H_2C$=CRCOA- in which R is H or $CH_3$ and A is O or NH.

28. A process according to claim 25 in which $R^{13}$ is a straight chain alkyl having 8 to 18 carbon atoms.

29. A process according to claim 28 in which $Y^1$ is $H_2C$=$CR^{14}COA^1$- in which $R^{14}$ is H or $CH_3$ and $A^1$ is O or NH.

30. A process according to claim 25 in which $R^{20}$ is trimethoxysilyl, $B^2$ is $C_{2-6}$ alkanediyl and $Y^2$ is $H_2C$=$CR^{21}COA^2$ in which $R^{21}$ is H or $CH_3$ and $A^2$ is O or NH.

31. A process according to claim 25 in which X is a group of formula VI:

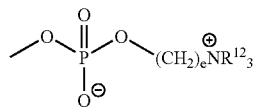

VI where the groups $R^{12}$ are the same or different and each is hydrogen or $C_{1-4}$ alkyl, and e is from 1 to 4;

B is $C_{2-6}$ alkanediyl;

Y is $H_2C$=CRCOA- in which R is H or $CH_3$ and A is O or NH;

$R^{13}$ is a straight chain alkyl having 8 to 18 carbon atoms;

$Y^1$ is $H_2C$—$CR^{14}COA^1$ in which $R^{14}$ is H or $CH_3$ and $A^1$ is O or NH;

$R^{20}$ is trimethoxysilyl, $B^2$ is $C_{2-6}$ alkanediyl; and $Y^2$ is $H_2C$—$CR^{21}COA^2$- in which $R^{21}$ is H or $CH_3$ and $A^2$ is O or NH.

32. A process according to claim 25 in which the thickness of the coating of polymer matrix of the sterile coated implant is in the range of 500 nm to 500 μm.

33. A process according to claim 25 in which step i) comprises the steps:

ia) providing a coating composition comprising cross-linkable polymer formed from ethylenically unsaturated monomers including said zwitterionic monomer, said surface binding monomer and said ractive monomer;

ib) coating the implant with the coating composition whereby an implant is coated with cross-linkable polymer; and ic) curing the cross-linkable polymer under conditions such that the trialkoxy silyl group $R^{20}$ form inter molecular cross-links to form a crosslinked polymer matrix coating.

34. A process according to claim 33 in which the implant is a vascular stent, having inner and outer surfaces.

35. A process according to claim 34 in which the outer surface of the stent is provided with a thicker coating of cross-linkable polymer than the inner surface in step ib).

36. A process for providing a pharmaceutical-loaded stent comprising the steps:

a) providing a stent comprising a generally tubular body formed of substantially impermeable biostable material and having interior and exterior surfaces;

b) providing the interior and exterior surfaces of the stent with a coating of cross-linkable polymer in such a manner that the outer surface of the stent is provided with a thicker coating of cross-linkable polymer than the inner surface, the ratio of the thickness of the coatings on the exterior and interior surfaces being (1.5-50):1 and the thickness of the biocompatible coating on the exterior surface is in the range 500 nm to 500 μm;

c) cross-linking the cross-linkable polymer to provide a cross-linked biostable polymer matrix coated stent;

d) sterilising the coated stent;

e) providing a pharmaceutical solution comprising a pharmaceutical active having molecular weight up to 1200 D in solution in a solvent which is capable of swelling the cross-linked polymer matrix of the sterilised stent coating;

f) contacting the coated sterilised stent with the pharmaceutical solution by dipping for a period in the range 30 seconds to 30 minutes, whereby the polymer matrix swells and pharmaceutical active is dispersed through the matrix to produce a pharmaceutical active loaded implant wherein the cross-linkable polymer is formed from ethylenically unsaturated monomers including a zwitterionic monomer and a reactive monomer;

wherein the said cross-linking involves reaction of the reactive monomer residues to form inter molecular cross-links; and wherein the cross-linked polymer is water-swellable and biocompatible.

37. A process according to claim 36 in which the thickness of the biocompatible coating on the exterior surface is in the range 500 nm to 5 μm.

38. A process according to claim 36 in which the solvent is selected from the group consisting of alcohols, glycols, water and mixtures thereof.

39. A process according to claim 38 in which the solvent comprises an alcohol which is a lower alkanol.

40. A process according to claim 36 in which the ethylenically unsaturated monomers include a surface binding monomer, selected from a hydrophobic comonomer, a reactive monomer having one or more pendant reactive groups capable of forming intermolecular cross-links, and mixtures thereof.

41. A process according to claim 36 in which the zwitterionic monomer has the general formula I:

YBX    I wherein

B is selected from the group consisting of straight and branched alkylene, alkyleneoxaalkylene and alkylene oligo-oxaalkylene chains optionally containing one or more fluorine atoms up to and including perfluorinated chains and, if X or Y contains a terminal carbon atom bonded to B, a valence bond;

X is a zwitterionic group; and

Y is an ethylenically unsaturated polymerisable group selected from the group consisting of

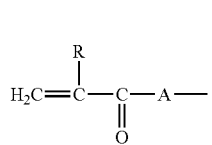 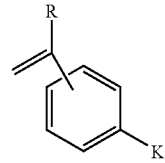

$CH_2=C(R)CH_2O-$, $CH_2=C(R)CH_2OC(O)-$, $CH_2=C(R)OC(O)-$, $CH_2=C(R)O-$, $CH_2=C(R)CH_2OC(O)N(R^1)-$, $R^2OOCCR=CRC(O)O-$, $RCH=CHC(O)O-$, $RCH=C(COOR^2)CH_2C(O)O-$,

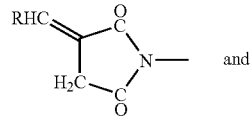 and 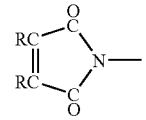

wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1-4}$ alkyl group;

A is —O— or —$NR^1$—;

K is selected from the group consisting of —$(CH_2)_pOC(O)—$, —$(CH_2)_pC(O)O—$, —$(CH_2)_pOC(O)O—$, —$(CH_2)_pNR^3—$, —$(CH_2)_pNR^3C(O)—$, —$(CH_2)_pC(O)NR^3—$, —$(CH_2)_pNR^3C(O)O—$, —$(CH_2)_pOC(O)NR^3—$, —$(CH_2)_pNR^3C(O)NR^3—$ (in which the groups $R^3$ are the same or different), —$(CH_2)_pO—$, —$(CH_2)_pSO_3—$, and, optionally in combination with B, a valence bond p is from 1 to 12; and $R^3$ is hydrogen or a $C_1$-$C_4$ alkyl group.

42. A process according to claim 41 in which X is a group of formula VI:

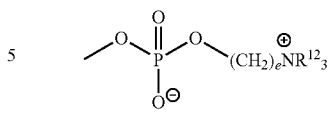    VI where the groups $R^{12}$ are the same or different and each is hydrogen or $C_{1-4}$ alkyl, and e is from 1 to 4.

43. A process according to claim 42 in which B is $C_{2-6}$ alkanediyl and Y is $H_2C=CRCOA$ in which R is H or $CH_3$ and A is O or NH.

44. A process according to claim 40 in which the surface binding monomer has the general formula VII $Y^1R^{13}$    VII wherein $Y^1$ is selected from the group consisting of

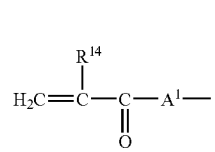 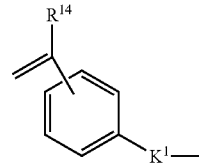

$CH_2=C(R^{14})CH_2O—$, $CH_2=C(R^{14})CH_2OC(O)—$, $CH_2=C(R^{14})OC(O)—$, $CH_2=C(R^{14})O—$, $CH_2=C(R^{14})CH_2OC(O)N(R^{15})—$, $R^{16}OOCCR^{14}=CR^{14}C(O)O—$, $R^{14}CH=CHC(O)O—$, $R^{14}CH=C(COOR^{16})CH_2C(O)—$,

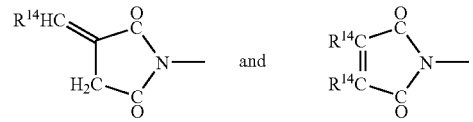 and 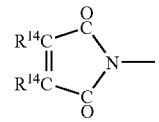

wherein:

$R^{14}$ is hydrogen or a $C_1$-$C_4$ alkyl group;

$R^{15}$ is hydrogen or a $C_1$-$C_4$ alkyl group or $R^{15}$ is $R^{13}$;

$R^{16}$ is hydrogen or a $C_{1-4}$ alkyl group;

$A^1$ is —O— or —$NR^{15}$—; and $K^1$ is selected from the group consisting of —$(CH_2)_qOC(O)—$, —$(CH_2)_qC(O)O—$, —$(CH_2)_qOC(O)O—$, —$(CH_2)_qNR^{17}—$, —$(CH_2)_qNR^{17}C(O)—$, —$(CH_2)_qC(O)NR^{17}—$, —$(CH_2)_qNR^{17}C(O)O—$, —$(CH_2)_qOC(O)NR^{17}—$, —$(CH_2)_qNR^{17}C(O)NR^{17}—$ (in which the groups $R^{17}$ are the same or different), —$(CH_2)_qO—$, —$(CH_2)_qSO_3—$, and a valence bond q is from 1 to 12;

and $R^{17}$ is hydrogen or a $C_1$-$C_4$ alkyl group;

and $R^{13}$ is a surface binding group, selected from hydrophobic groups and ionic groups.

45. A process according to claim 44 in which $R^{13}$ is a straight chain alkyl having 8 to 18 carbon atoms.

46. A process according to claim 45 in which $Y^1$ is $H_2C=CR^{14}COA^1$ in which $R^{14}$ is H or $CH_3$ and $A^1$ is O or NH.

47. A process according to claim 40 in which the reactive monomer has the general formula VIII $Y^2B^2R^{20}$    VIII wherein
- $B^2$ is selected from the group consisting of straight or branched alkylene, oxaalkylene and oligo-oxaalkylene chain optionally containing one or more fluorine atoms up to and including perfluorinated chains, and a valence bond;
- $Y^2$ is an ethylenically unsaturated polymerisable group selected from the group consisting of

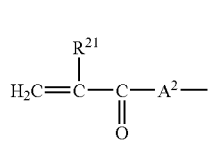 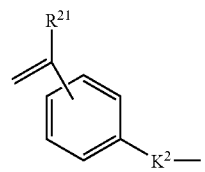

$CH_2=C(R^{21})CH_2—O—$, $CH_2=C(R^{21})CH_2OC(O)—$, $CH_2=C(R^{21})OC(O)—$, $CH_2=C(R_{21})O—$, $CH_2=C(R^{21})CH_2OC(O)N(R^{22})—$, $R^{23}OOCCR^{21}=CR^{21}C(O)O—$, $R^{21}H=CHC(O)O—$, $R^{21}H=C(COOR^{23})CH_2C(O)O—$

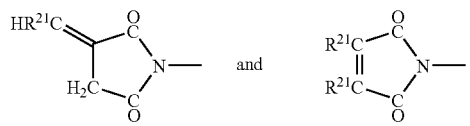

where
- $R^{21}$ is hydrogen or $C_1$-$C_4$ alkyl;
- $R^{23}$ is hydrogen, or a $C_{1-4}$ alkyl group;
- $A^2$ is —O— or —$NR^{22}$—;
- $R^{22}$ is hydrogen or a $C_1$-$C_4$ alkyl group or $R^{22}$ is a group $B^2R^{20}$;
- $K^2$ is selected from the group consisting of —$(CH_2)_kOC(O)$—, —$(CH)_kC(O)O$—, —$(CH_2)_kOC(O)O$—, —$(CH_2)_kNR^{22}$—, —$(CH_2)_kNR^{22}C(O)$—, —$(CH_2)_kOC(O)O$—, —$(CH_2)_kNR^{22}$—, —$(CH_2)_kNR^{22}C(O)$—, —$(CH_2)_kC(O)NR^{22}$—, —$(CH_2)_kNR^{22}C(O)O$—, —$(CH_2)_kOC(O)NR^{22}$—, —$(CH_2)_kNR^{22}C(O)NR^{22}$— (in which the groups $R^{22}$ are the same or different), —$(CH_2)_kO$—, —$(CH_2)_kSO_3$—, and a valence bond and k is from 1 to 12; and
- $R^{20}$ is a cross-linkable group.

48. A process according to claim 47 in which $R^{20}$ is selected from the group consisting of ethylenically and acetylenically unsaturated groups containing radicals; aldehyde groups; silane and siloxane groups containing one or more substituents selected from halogen atoms and $C_{1-4}$ alkoxy groups; hydroxyl; amino; carboxyl; epoxy; —$CHOHCH_2Hal$ (in which Hal is selected from chlorine, bromine and iodine atoms); succinimido; tosylate; triflate; imidazole carbonyl amino; optionally substituted triazine groups; acetoxy; mesylate; carbonyl di(cyclo)alkyl carbodiimidoyl; isocyanate, acetoacetoxy; and oximino.

49. A process according to claim 48 in which $R^{20}$ comprises a silane group containing at least one substituent selected from halogen atoms and $C_{1-4}$ alkoxy groups.

50. A process according to claim 49 in which $R^{20}$ is trimethoxysilyl, $B^2$ is $C_{2-6}$ alkanediyl and $Y^2$ is $H_2C=CR^{21}COA^2$- in which $R^{21}$ is H or $CH_3$ and $A^2$ is O or NH.

51. A process according to claim 36 wherein each biocompatible coating is 500 nm to 5 μm thick.

52. A process for producing an implant loaded with a pharmaceutically active agent comprising the steps:
a) providing a sterile coated implant comprising a biostable implant and a coating comprising a polymer matrix that is covalently cross-linked and/or bound to the implant surface and has pendant zwitterionic groups, wherein the polymer matrix is formed from cross-linked polymer formed from ethylenically unsaturated monomers consisting of a zwitterionic monomer, a surface binding monomer, and optional reactive monomer and diluent comonomer, wherein the zwitterionic monomer has the general formula I:

$$YBX \qquad\qquad I$$

wherein
- B is selected from the group consisting of straight and branched alkylene, alkylene-oxaalkylene and alkylene oligo-oxaalkylene chains optionally containing one or more fluorine atoms up to and including perfluorinated chains and, if X or Y contains a terminal carbon atom bonded to B, a valence bond;
- X is a zwitterionic group of the general formula V

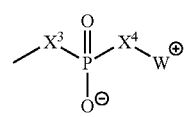

in which $X^3$ and $X^4$, which are the same or different, are selected from the group consisting of —O—, —S—, —NH— and a valence bond, and
- $W^+$ is selected from the group consisting of —$W^1$—$N^+R^{11}_3$, —$W^1$—$P^+R^{11}_3$, —$W^1$—$S^+R^{11}_2$ or —$W^1$-$Het^+$ in which:
- $W^1$ is selected from the group consisting of alkanediyl of 1-6 carbon atoms optionally containing one or more ethylenically unsaturated double or triple bonds, disubstituted-aryl, alkylene aryl, aryl alkylene, alkylene aryl alkylene, disubstituted cycloalkyl, alkylene cycloalkyl, cycloalkyl alkylene and alkylene cycloalkyl alkylene, which group $W^1$ optionally contains one or more fluorine substituents and/or one or more functional groups; and
- either groups $R^{10}$ are the same or different and each is selected from the group consisting of hydrogen, alkyl of 1 to 4 carbon atoms and aryl, or two of the groups $R^{10}$ together with the nitrogen atom to which they are attached form a heterocyclic ring containing from 5 to 7 atoms or three groups $R^{10}$ together with the nitrogen atom to which they are attached form a fused ring structure containing from 5 to 7 atoms in each ring, and optionally one or more of the groups $R^{10}$ is substituted by a hydrophilic functional group, and
- the groups $R^{11}$ are the same or different and each is $R^{10}$ or a group $OR^{10}$, where $R^{10}$ is as defined above; and
- Het is selected from the group consisting of aromatic nitrogen-, phosphorus- and sulphur-containing rings; and
- Y is an ethylenically unsaturated polymerisable group selected from the group consisting of

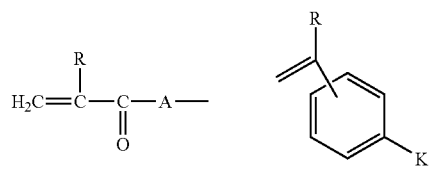

$CH_2$=$C(R)CH_2O$—, $CH_2$=$C(R)CH_2OC(O)$—, $CH_2$=$C(R)OC(O)$—, $CH_2$=$C(R)O$—, $CH_2$=$C(R)CH_2OC(O)N(R^1)$—, $R^2OOCCR$=$CRC(O)O$—, $RCH$=$CHC(O)O$—, $RCH$=$C(COOR^2)CH_2C(O)O$—,

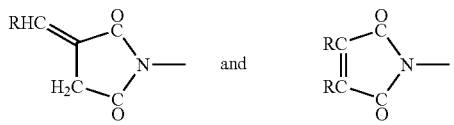

wherein
R is hydrogen or a $C_1$-$C_4$ alkyl group;
$R^1$ is hydrogen or a $C_1$-$C_4$ alkyl group or $R^1$ is —B—X where B and X are as defined above; and
$R^2$ is hydrogen or a $C_{1-4}$ alkyl group;
A is —O— or $NR^1$—;
K is selected from the group consisting of —$(CH_2)_pOC(O)$—, —$(CH_2)_pC(O)O$—, —$(CH_2)_pOC(O)O$—, —$(CH_2)_pNR^3$, —$(CH_2)_pNR^3C(O)$—, —$(CH_2)_pC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, and, optionally in combination with B, a valence bond;
p is from 1 to 12; and
$R^3$ is hydrogen or a $C_1$-$C_4$ alkyl group, and
wherein the surface binding monomer has the general formula VII $Y^1R^{13}$     VII wherein $Y^1$ is selected from the group consisting of

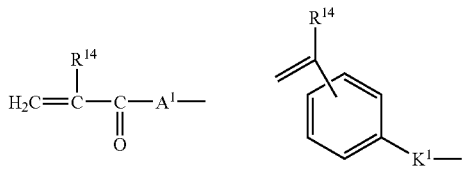

$CH_2$=$C(R^{14})CH_2O$—, $CH_2$=$C(R^{14})CH_2OC(O)$—, $CH_2$=$C(R^{14})OC(O)$—, $CH_2$=$C(R^{14})O$—, $CH_2$=$C(R^{14})CH_2OC(O)N(R^{15})$—, $R^{16}OOCCR^{14}$=$CR^{14}C(O)O$—, $R^{14}CH$=$CHC(O)O$—, $R^{14}CH$=$C(COOR^{16})CH_2C(O)$—$O$—,

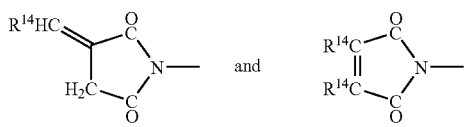

wherein:
$R^{14}$ is hydrogen or a $C_1$-$C_4$ alkyl group;
$R^{15}$ is hydrogen or a $C_1$-$C_4$ alkyl group or $R^{15}$ is $R^{13}$;
$R^{16}$ is hydrogen or a $C_{1-4}$ alkyl group;
$A^1$ is —O— or —$NR^{15}$—; and
$K^1$ is selected from the group consisting of —$(CH_2)_qOC(O)$—, —$(CH_2)_qC(O)O$—, —$(CH_2)_qOC(O)O$—, —$(CH_2)_qNR^{17}$, —$(CH_2)_qNR^{17}C(O)$—, —$(CH_2)_qC(O)NR^{17}$—, —$(CH_2)_qNR^{17}C(O)O$—, —$(CH^2)_qOC(O)NR^{17}$—, —$(CH_2)_qNR^{17}C(O)NR^{17}$— (in which the groups $R^{17}$ are the same or different), —$(CH_2)_qO$—, —$(CH_2)_qSO_3$—, and a valence bond;
q is from 1 to 12;
and $R^{17}$ is hydrogen or a $C_1$-$C_4$ alkyl group;
and $R^{13}$ is a surface binding group, selected from hydrophobic groups and cross-linkable groups $B^2R^{20}$;
wherein
$B^2$ is selected from the group consisting of straight or branched alkylene, oxaalkylene and oligo-oxaalkylene chain optionally containing one or more fluorine atoms up to and including perfluorinated chains, and a valence bond; and
$R^{20}$ is a cross-linkable group selected from the group consisting of ethylenically and acetylenically unsaturated groups containing radicals; aldehyde groups; silane and siloxane groups containing one or more substituents selected from halogen atoms and $C_{1-4}$ alkoxy groups; hydroxyl; amino; carboxyl; epoxy; —$CHOHCH_2Hal$ (in which Hal is selected from chlorine, bromine and iodine atoms); succinimido; tosylate; triflate; imidazole carbonyl amino; optionally substituted triazine groups, acetoxy; mesylate; carbonyl di(cyclo)alkyl carbodiimidoyl; isocyanate, acetoacetoxy; and oximino; and
wherein the diluent monomer is a nonionic monomer;
b) providing a pharmaceutical solution comprising a pharmaceutically active agent in solution in a solvent, wherein the pharmaceutically active agent has a molecular weight of up to 1200 D and the solvent is capable of swelling the said coating; and
c) contacting the coated implant with the pharmaceutical solution at a temperature and for a time to allow swelling of the coating and dispersal of active through the polymer matrix to produce a pharmaceutically active loaded implant.

53. A process according to claim 52 in which the polymer matrix is substantially non-biodegradable.

54. A process according to claim 52 wherein providing the sterile coated implant comprises:
   a1) coating a biostable implant with a coating composition containing the polymer of the matrix, or a precursor thereof,
   a2) curing the polymer to form the said polymer matrix; and
   a3) sterilising the implant coated with the polymer matrix.

55. A process according to claim 52 in which the coating composition contains a cross-linkable polymer and in which curing involves cross-linking the polymer.

56. A process according to claim 52 in which $R^{13}$ is a straight chain alkyl having 8 to 18 carbon atoms.

57. A process according to claim 52 in which $R^{20}$ comprises a silane group containing at least one substituent selected from halogen atoms and $C_{1-4}$-alkoxy groups.

58. A process according to claim 52 in which $R^{20}$ is a trimethoxysilyl group.

59. A process according to claim 52 in which the thickness of the coating of polymer matrix of the sterile coated implant is in the range 500 nm to 500 μm.

60. A process according to claim 52 in which both inner and outer surfaces of the stent are coated with polymer matrix and both polymer coated surfaces are contacted with pharmaceutical solution in step c).

61. A process according to claim 52 in which the ratio of thickness of polymer matrix on the outer to the inner surface is (at least 1.5):1.

62. A process according to claim 52 in which the pharmaceutically active agent is selected from the group consisting of dipyridamole, angiopeptin, taxol, roxithromycin, rapamycin, tetradecylthioacetic acid, aspirin, etoposide and dexamethasone.

* * * * *